United States Patent [19]

Sakaguchi et al.

[11] Patent Number: 5,646,184
[45] Date of Patent: Jul. 8, 1997

[54] PREPARATION FOR EXTERNAL APPLICATION TO THE SKIN AND NOVEL BENZOIC ACID DERIVATIVES

[75] Inventors: Akira Sakaguchi, Wakayama; Takashi Kitahara, Tochigi; Keiko Koizumi, Tochigi; Noriko Sato, Tochigi; Kimihiko Hori, Tochigi; Hiroyuki Shinta, Tochigi, all of Japan

[73] Assignee: Kao Corporation, Tokyo, Japan

[21] Appl. No.: 335,854

[22] PCT Filed: Mar. 25, 1994

[86] PCT No.: PCT/JP94/00477

§ 371 Date: Nov. 9, 1994

§ 102(e) Date: Nov. 9, 1994

[87] PCT Pub. No.: WO94/21591

PCT Pub. Date: Sep. 29, 1994

[30] Foreign Application Priority Data

Mar. 25, 1993 [JP] Japan .................. 5-066779
Dec. 15, 1993 [JP] Japan .................. 5-315606

[51] Int. Cl.$^6$ .............. A61K 31/235; A61K 31/19; A61K 31/165
[52] U.S. Cl. .............. 514/543; 514/568; 514/622; 560/43; 560/61; 562/433; 562/471; 564/163; 564/167; 564/170; 564/176; 564/177
[58] Field of Search .............. 560/43, 61; 562/433, 562/471; 564/163, 167, 170, 176, 177; 514/543, 568, 622

[56] References Cited

U.S. PATENT DOCUMENTS

| | | | |
|---|---|---|---|
| 3,712,913 | 1/1973 | Subraya | 560/18 |
| 4,616,090 | 10/1986 | Jonas | 558/397 |
| 4,771,034 | 9/1988 | Ikeda et al. | 503/212 |
| 5,104,881 | 4/1992 | Jonas et al. | 514/303 |

FOREIGN PATENT DOCUMENTS

| | | |
|---|---|---|
| 0072926 | 7/1982 | European Pat. Off. . |
| 0225189 | 6/1987 | European Pat. Off. . |
| 0570230 | 11/1993 | European Pat. Off. . |
| 1153616 | 6/1989 | Japan . |
| 63-286606 | 6/1989 | Japan . |
| 08002295 | 1/1991 | Japan . |

OTHER PUBLICATIONS

Abstract of Japanese Patent No. 55-334.
Abstract of Japanese Patent No. 5-100436.
Abstract of Japanese Patent No. 63-22682.
Dadgar, et al. J. Chromatogr. 324(2) 315–21.
Rangaswami, et al. Arch. Pharm. 292, 170–6 (1959) **[CA53:21919e].
Maeda, T. et al., Effects of royal jelly and 10-hydroxydecenoic acid on the sebaceous glands of hamster ear, Hifuka Gakkai Zasshi 1988, 98 (4), pp. 469–475 (Japan) and English Abstract.

*Primary Examiner*—Joseph Conrad
*Attorney, Agent, or Firm*—Birch, Stewart, Kolasch & Birch, LLP

[57] ABSTRACT

Disclosed is a preparation for external application to the skin characterized by containing at least one of benzoic acid derivatives represented by formula (I) or pharmacologically acceptable salts thereof as an active ingredient, the preparation having sufficient sebaceous secretion inhibitory activity with no substantial side effect and high safety for human body.

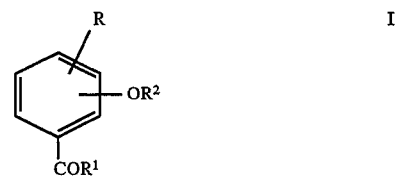

wherein $R^1$ represents —OH, —OR$^3$ or —NHR$^3$; $R^2$ represents a hydrogen atom, a lower alkyl group or a lower acyl group; R represents —O—R$^4$ or

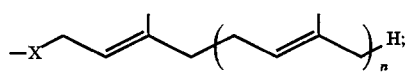

$R^3$ represents an alkyl group, an alkenyl group or a hydroxyalkyl group; $R^4$ represents a straight-chain or branched, saturated or mono-unsaturated alkyl group or cycloalkylalkyl group having from 4 to 10 carbon atoms; X represents —O— or —NH—; and n represents 1 or 2.

32 Claims, No Drawings

PREPARATION FOR EXTERNAL APPLICATION TO THE SKIN AND NOVEL BENZOIC ACID DERIVATIVES

FIELD OF THE INVENTION

This application is a 371 of PCT/JP94/00477 filed Mar. 25, 1994.

This invention relates to a preparation for external application to the skin containing a benzoic acid derivative having sebaceous secretion inhibitory activity with high safety for human body and to novel benzoic acid derivatives.

BACKGROUND OF THE INVENTION

Known sebaceous secretion inhibiting agents include anti-male sex hormone agents, vitamin A acid, royal jelly acid [Nichihi Kaishi, Vol. 98, No. 4, pp. 469–475 (1988)], and p-hydroxybenzoic acid derivatives (Japanese Patent Public Disclosure No. 153616/89).

The anti-male sex hormone agent is a substance relative to hormone metabolism, and vitamin A acid also has a hormone-like action. Exerting their action on not only sebaceous glands but other organs, these agents give rise to a great problem of systemic side effects rather than producing topical effects. Royal jelly acid and the conventional p-hydroxybenzoic acid derivatives were insufficient in their effects.

Accordingly, a primary object of the present invention is to provide a preparation for external application to the skin which exhibits sufficient inhibitory activity on sebaceous secretion and is of high safety for human body causing no side effects.

A secondary object of the present invention is to provide a novel benzoic acid derivative which is useful as an active ingredient of the above-mentioned preparation.

DISCLOSURE OF THE INVENTION

The present inventors have conducted extensive investigations into sebaceous secretion inhibiting agents by which the above objects of the present invention can be accomplished. As a result, they have found that specific benzoic acid derivatives have a high sebaceous secretion inhibitory effect and also discovered novel benzoic acid derivatives. The present invention has been completed based on these findings.

The present invention provides a preparation for external application to the skin characterized by containing at least one of benzoic acid derivatives represented by general formula (I) shown below or pharmacologically acceptable salts thereof as an active ingredient:

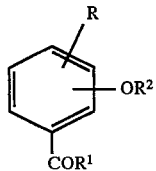

wherein $R^1$ represents —OH, —OR$^3$ or —NHR$^3$; $R^2$ represents a hydrogen atom, a lower alkyl group or a lower acyl group; R represents —O—R$^4$ or

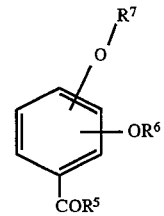

$R^3$ represents an alkyl group, an alkenyl group or a hydroxyalkyl group; $R^4$ represents a straight-chain or branched, saturated or mono-unsaturated alkyl group or cycloalkylalkyl group having from 4 to 10 carbon atoms; X represents —O— or —NH—; and n represents 1 or 2.

The present invention also provides a novel benzoic acid derivative represented by formula (II) shown below and a pharmacologically acceptable salt thereof:

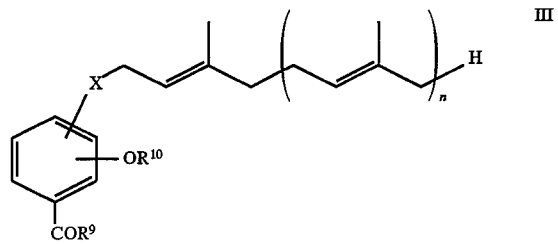

wherein $R^5$ represents —OH, —OR$^8$ or —NHR$^8$; $R^6$ represents a hydrogen atom, a lower alkyl group or a lower acyl group; $R^7$ represents a branched saturated or mono-unsaturated alkyl group or cycloalkylalkyl group having from 6 to 10 carbon atoms; and $R^8$ represents an alkyl group or a hydroxyalkyl group.

The present invention further provides a novel benzoic acid derivative represented by formula (III) shown below and a pharmacologically acceptable salt thereof:

wherein $R^9$ represents —OH, —OR$^{11}$ or —NHR$^{11}$; $R^{10}$ represents a hydrogen atom, a lower alkyl group or a lower acyl group; $R^{11}$ represents an alkyl group, an alkenyl group or a hydroxyalkyl group; X represents —O— or —NH—; and n represents 1 or 2.

BEST EMBODIMENT FOR CARRYING OUT THE INVENTION

The preparation for external application to the skin according to the present invention will be illustrated in more detail.

The benzoic acid derivative which can be used as an active ingredient of the preparation is represented by formula (I).

In formula (I), the lower alkyl group as represented by $R^2$ preferably includes those having 1 to 5 carbon atoms, such as a methyl group, an ethyl group, an isopropyl group, a butyl group, and a pentyl group. The lower acyl group as represented by $R^2$ preferably includes those having 1 to 6 carbon atoms, such as a formyl group, an acetyl group, a propionyl group, and a hexanoyl group.

The alkyl group as represented by $R^3$ preferably includes a methyl group, an ethyl group, an isopropyl group, a butyl group, and a pentyl group. The alkenyl group as represented by $R^3$ preferably include those having 1 to 20 carbon atoms, such as a (2E)-3,7-dimethylocta-2,6-dienyl group and a (2E,6E)-3,7,11-trimethyl-2,6,10-dodecatrienyl group. The hydroxyalkyl group as represented by $R^3$ preferably includes a hydroxymethyl group, a 2-hydroxyethyl group, a 1-hydroxyethyl group, a 3-hydroxypropyl group, and a 5-hydroxypentyl group.

$R^4$ represents a straight-chain or branched saturated or mono-unsaturated alkyl or cycloalkylalkyl group having 4 to 10 carbon atoms, preferably 5 to 10 carbon atoms. Suitable examples of $R^4$ are an n-hexyl group, an n-octyl group, an n-decyl group, a 2-ethylhexyl group, a 3-methylbutyl group, a 3,3,5-trimethylhexyl group, a cyclohexylmethyl group, a cyclohexylethyl group, a 3,7-dimethyl-6-octenyl group, and a 3-methyl-2-butenyl group.

The pharmacologically acceptable salt of the above-described benzoic acid derivative (hereinafter referred to as a benzoic acid derivative salt), which can be used as an active ingredient of the preparation of the present invention, is a salt formed between the above benzoic acid derivative and an arbitrary base.

Examples of the base include alkali metals, e.g., sodium and potassium; alkaline earth metals; ammonium; alkanolamines, e.g., triethanolamine; and basic amino acids, e.g., lysine and arginine.

Accordingly, the benzoic acid derivative salt includes an alkali metal salt (e.g., a sodium salt or a potassium salt), an alkaline earth metal salt, an ammonium salt, an alkanolamine salt (e.g., a triethanolamine salt), and a basic amino acid salt (e.g., a lysine salt or an arginine salt) of the above benzoic acid derivative.

The benzoic acid derivative salt is a salt formed by introducing the above-mentioned base into the position(s) (substituent(s)) of —$COR^1$ and/or —$OR^2$, preferably the position of —$COR^1$, in formula (I) wherein $R^1$ is —OH, and $R^2$ is a hydrogen atom.

The benzoic acid derivative salt can be prepared either by starting with a material previously converted into its salt in the processes hereinafter described or by introducing a salt forming step into the course of the processes described.

Where R in formula (I) is —O—$R^4$, preferred positional relationships among the substituents are shown in formulae (a) and (b):

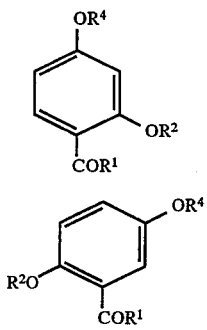

Specific examples of the benzoic acid derivatives represented by formula (I) include methyl 4-(2-ethylhexyloxy)-2-hydroxybenzoate, methyl 2-hydroxy-4-(3,5,5-trimethylhexyloxy)benzoate, methyl 4-cyclohexylmethoxy-2-hydroxybenzoate, methyl 4-(2-cyclohexylethoxy)-2-hydroxybenzoate, methyl 4-(3,7-dimethyl-6-octenyloxy)-2-hydroxybenzoate, ethyl 3-(2-ethylhexyloxy)-5-hydroxybenzoate, methyl 5-(2-ethylhexyloxy)-2-hydroxybenzoate, methyl 2-hydroxy-5-(3,5,5-trimethylhexyloxy)benzoate, methyl 5-(2-cyclohexylethoxy)- 2-hydroxybenzoate, methyl 4-n-hexyloxy-2-hydroxybenzoate, methyl 2-hydroxy-4-n-octyloxybenzoate, methyl 4-n-decyloxy-2-hydroxybenzoate, methyl 5-n-hexyloxy-2-hydroxybenzoate, 4-(2-ethylhexyloxy)-2-hydroxybenzoic acid, 2-hydroxy-4-(3,5,5-trimethylhexyloxy)benzoic acid, 4-cyclohexylmethoxy-2-hydroxybenzoic acid, 4-(2-cyclohexylethoxy)-2-hydroxybenzoic acid, 4-(3,7-dimethyl-6-octenyloxy)-2-hydroxybenzoic acid, 3-(2-ethylhexyloxy)-5-hydroxybenzoic acid, 5-(2-ethylhexyloxy)-2-hydroxybenzoic acid, 2-hydroxy-5-(3,5,5-trimethylhexyloxy)benzoic acid, 5-(2-cyclohexylethoxy)-2-hydroxybenzoic acid, 4-n-hexyloxy-2-hydroxybenzoic acid, 5-n-hexyloxy-2-hydroxybenzoic acid, 2-hydroxy-4-n-octyloxybenzoic acid, 4-n-decyloxy-2-hydroxybenzoic acid, N-(2-hydroxyethyl)-4-(2-ethylhexyloxy)-2-hydroxybenzamide, N-ethyl-4-(2-ethylhexyloxy)-2-hydroxybenzamide, 2-acetoxy-4-cyclohexylmethoxybenzoic acid, sodium 4-(2-ethylhexyloxy)-2-hydroxybenzoate, methyl 4-{(2E)-3,7-dimethylocta-2,6-dienyloxy}-2-hydroxybenzoate, ethyl 4-{(2E))-3,7-dimethylocta-2,6-dienyloxy}-2-hydroxybenzoate, ethyl 5-{(2E)-3,7-dimethylocta-2,6-dienyloxy}-2-hydroxybenzoate, ethyl 3-{(2E)-3,7-dimethylocta-2,6-dienyloxy}-2-hydroxybenzoate, ethyl 3-{(2E)-3,7-dimethylocta-2,6-dienyloxy}-5-hydroxybenzoate, ethyl 4- {(2E)-3,7-dimethylocta-2,6-dienyloxy}-3-methoxybenzoate, methyl 4-{(2E,6E)-3,7,11-trimethyl-2,6,10-dodecatrienyloxy}-2-hydroxybenzoate, (2E)-3,7-dimethylocta-2,6-dienyl 4-{(2E)-3,7-dimethylocta-2,6-dienyloxy}-2-hydroxybenzoate, 4-{(2E)-3,7-dimethylocta-2,6-dienyloxy}-2-hydroxybenzoic acid, 5-{(2E)-3,7-dimethylocta-2,6-dienyloxy}-2-hydroxybenzoic acid, 3- {(2E)-3,7-dimethylocta-2,6-dienyloxy}-2-hydroxybenzoic acid, 3-{(2E)-3,7-dimethylocta-2,6-dienyloxy}-5-hydroxybenzoic acid, 2-hydroxy-4-{(2E,6E)-3,7,11-trimethyl-2,6,10-dodecatrienyloxy}benzoic acid, 4-{(2E)-3,7-dimethylocta-2,6-dienyloxy}-3-methoxybenzoic acid, 2-acetoxy-4-{(2E)-3,7-dimethylocta-2,6-dienyloxy}benzoic acid, N-(2-hydroxyethyl)-4-{(2E)-3,7-dimethylocta-2,6-dienyloxy}-2-hydroxybenzamide, and N-{(2E)-3,7-dimethylocta-2,6-dienyl}-4-amino-2-hydroxybenzoic acid.

Of the benzoic acid derivatives represented by formula (I) preferred are 4-(2-ethylhexyloxy)-2-hydroxybenzoic acid, 2-hydroxy-4-(3,5,5-trimethylhexyloxy)benzoic acid, 4-(2-cyclohexylethoxy)-2-hydroxybenzoic acid, 4-n-hexyloxy-2-hydroxybenzoic acid, 5-(2-ethylhexyloxy)-2-hydroxybenzoic acid, 2-(hydroxy-5-(3,5,5-trimethylhexyloxy)benzoic acid, 5-(2-cyclohexylethoxy)-2-hydroxybenzoic acid, 5-n-hexyloxy-2-hydroxybenzoic acid, methyl 4-{(2E)-3,7-dimethylocta-2,6-dienyloxy}-2-hydroxybenzoate, ethyl 4-{(2E)-3,7-dimethylocta-2,6-dienyloxy}-2-hydroxybenzoate, ethyl 5-{(2E)-3,7-dimethylocta-2,6-dienyloxy}-2-hydroxybenzoate, ethyl 3-{(2E)-3,7-dimethylocta-2,6-dienyloxy}-2-hydroxybenzoate, ethyl 3-{(2E)-3,7-dimethylocta-2,6-dienyloxy}-5-hydroxybenzoate, ethyl 4-{(2E)-3,7-dimethylocta-2,6-dienyloxy}-3-methoxybenzoate, methyl 4-{(2E,6E)-3,7,11-trimethyl-2,6,10-dodecatrienyloxy}-2-hydroxybenzoate, (2E)-3,7-dimethylocta-2,6-dienyl 4-{(2E) -3,7-dimethylocta-2,6-dienyloxy}-2-hydroxybenzoate, 4-{(2E)- 3,7-dimethylocta-2,6-dienyloxy}-2-hydroxybenzoic acid, 5-{(2E)-3,7-dimethylocta-2,6-dienyloxy}-2-hydroxybenzoic acid, 3-{(2E)-3,7-dimethylocta-2,6-dienyloxy}-2-hydroxybenzoic acid, 3-{(2E)-3,7-dimethylocta-2,6-dienyloxy}-5-hydroxybenzoic acid, 2-hydroxy-4-{(2E,6E)-3,7,11-trimethyl-2,6,10-dodecatrienyloxy}benzoic acid, 4-{(2E)-3,7-dimethylocta-2,6-dienyloxy}-3-methoxybenzoic acid, 2-acetoxy-4-{(2E)-3,7-dimethylocta-2,6-dienyloxy}benzoic acid, N-(2-hydroxyethyl)-4-{(2E)-3,7-dimethylocta-2,6-dienyloxy}-2-hydroxybenzamide, and N-{(2E)-3,7-dimethylocta-2,6-dienyl}-4-amino-2-hydroxybenzoic acid.

The benzoic acid derivatives represented by formula (I) can easily be obtained by processes (1) to (9) described below, but the processes for preparing the benzoic acid derivatives are not limited thereto.

(1) Process for preparing benzoic acid derivatives (VI) (the compounds of formula (I) in which —COR$^1$ is an ester group (—COOR$^3$), and R is —O—R$^4$):

Benzoic acid derivative (VI) can be obtained by reacting compound (IV) and compound (V) in the presence or absence of a base in accordance with the following reaction formula.

The reaction is preferably carried out by using 0.5 to 3.0 mol of compound (V) per mole of compound (IV) at a temperature usually of from 0° to 150° C., preferably of from 20° to 100° C., for several hours while stirring. Any base can be used as long as no adverse influence is given to the reaction. Examples of suitable bases are sodium hydride, sodium amide, potassium carbonate, sodium carbonate, potassium hydroxide, and sodium hydroxide. Any solvent inert to the reaction can be used in the reaction. For example, N,N-dimethylformamide, dimethyl sulfoxide, tetrahydrofuran, ethanol, methanol or acetone is suitably used. After completion of the reaction, the solvent is removed by distillation, and the residue is purified by chromatography or a like means to isolate benzoic acid derivative (VI).

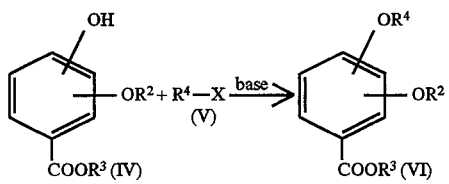

wherein R$^2$, R$^3$, and R$^4$ are as defined above; and X represents a releasable group, such as a halogen atom, a tosyl group or a mesyl group.

(2) Process for preparing benzoic acid derivatives (VII) (the compounds of formula (I) in which R$^1$ is —OH, R$^2$ is a hydrogen atom, and R is —O—R$^4$):

Benzoic acid derivative (VII) having a free carboxyl group can be obtained by hydrolyzing benzoic acid derivative (VI) using 1.0 to 3.0 mol of a base, such as sodium hydroxide or potassium hydroxide, per mol of benzoic acid derivative (VI) at 20° to 100° C. for several hours with stirring in accordance with the following reaction formula. Any solvent inert to the reaction can be used for the reaction. For example, N,N-dimethylformamide, dimethyl sulfoxide, ethanol, methanol, acetone or water is suitably used. These solvents may be used either individually or as a mixture thereof.

After completion of the reaction, the reaction product is purified by recrystallization, chromatography or a like means to isolate benzoic acid derivative (VII).

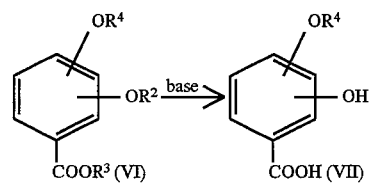

wherein R$^2$, R$^3$, and R$^4$ are as defined above.

(3) Process for preparing benzoic acid derivatives (VIII) (the compounds of formula (I) in which R$^1$ is —OH, R$^2$ is a lower acyl group, and R is —O—R$^4$):

Benzoic acid derivative (VIII), which is an O-acyl compound, can be obtained by reacting benzoic acid derivative (VII) with an acid anhydride or an acid halide in the presence of a base in accordance with the following reaction formula. Any base can be used as long as no adverse influence is exerted on the reaction. Examples of suitable bases are pyridine and triethylamine.

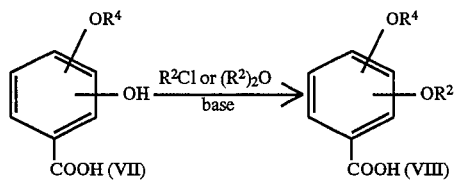

wherein R$^4$ is as defined above; and R$^2$ represents a lower acyl group.

(4) Process for preparing benzoic acid derivatives (IX) (the compounds of formula (I) in which R$^2$ is a hydrogen atom; R$^1$ is —NHR$^3$; and R is —O—R$^4$):

Benzoic acid derivative (IX), the compound of formula (I) in which R$^2$ is a hydrogen atom and R$^1$ is —NHR$^3$, can be obtained by treating a benzoic acid derivative shown in the following reaction formula with an acid halogenating agent, such as thionyl chloride, and then reacting with a primary amine in the presence of a base in accordance with the following reaction formula:

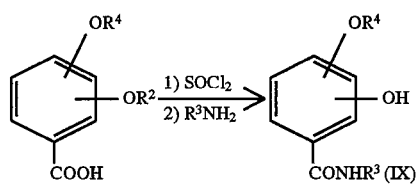

wherein R$^3$ and R$^4$ are as defined above; and R$^2$ represents a hydrogen atom or a lower acyl group.

(5) Process for preparing benzoic acid derivatives (X) [the compounds of formula (I) in which —COR$^1$ is an ester group (—COOR$^3$), and R is

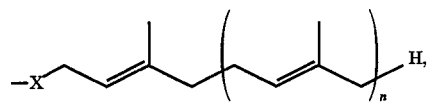

wherein X is an oxygen atom (—O—)]:

Benzoic acid derivative (X) can be obtained by reacting alkenyl halide (XI) with compound (XII) in the presence or absence of a base in accordance with the following reaction formula.

The above reaction is preferably carried out by using 0.5 to 3.0 mol of compound (XI) per mole of compound (XII)

at a temperature of from −20° to 200° C., preferably from 0° to 80° C., for several hours with stirring.

Any base can be used as long as the reaction is not adversely influenced. Examples of suitable bases are sodium hydride, sodium amide, potassium carbonate, sodium carbonate, potassium hydroxide, and sodium hydroxide. Any solvent inert to the reaction can be used in the reaction. For example, N,N-dimethylformamide, dimethyl sulfoxide, tetrahydrofuran, ethanol, methanol is suitably used.

After completion of the reaction, the solvent is removed by distillation, and the residue is purified by chromatography or a like means to isolate benzoic acid derivative (X).

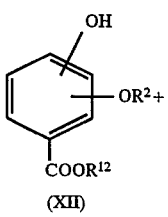
(XII)

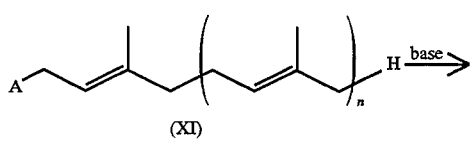
(XI)

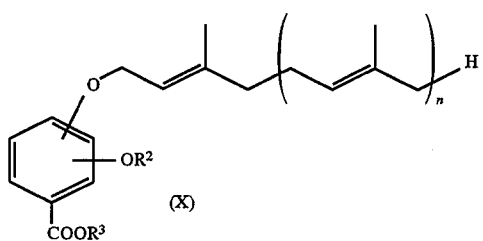
(X)

wherein n, $R^2$, and $R^3$ are as defined above; $R^{12}$ represents a hydrogen atom, an alkyl group, an alkenyl group or a hydroxyalkyl group; and A represents a halogen atom.

(6) Process for preparing benzoic acid derivatives (XIII) [the compounds of formula (I) in which $R^1$ is —OH, $R^2$ is a hydrogen atom, and R is

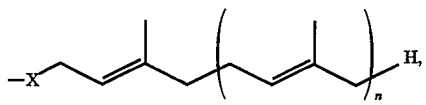

wherein X is an oxygen atom]

Benzoic acid derivative (XIII) having a free carboxyl group can be obtained by hydrolyzing benzoic acid derivative (X) using 1.0 to 3.0 mol of a base, such as sodium hydroxide or potassium hydroxide, at 20° to 100° C. for several hours with stirring.

Any solvent inert to the reaction can be used for the reaction. For example, N,N-dimethylformamide, dimethyl sulfoxide, ethanol, methanol or water is suitably used.

After completion of the reaction, the reaction product is purified by recrystallization, chromatography or a like means to isolate benzoic acid derivative (XIII).

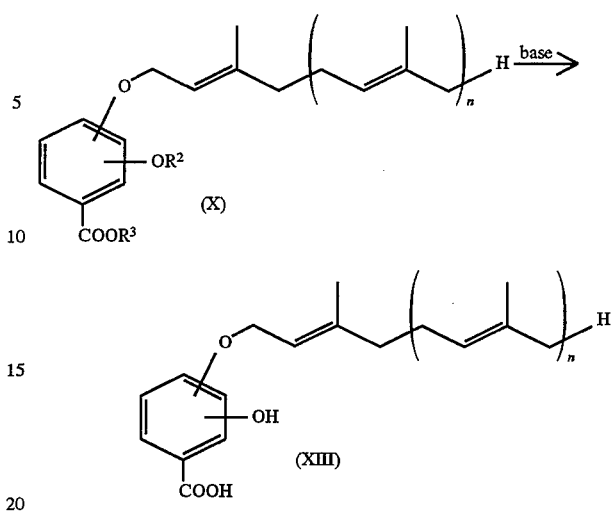
(X)

(XIII)

wherein n, $R^2$, and $R^3$ are as defined above.

(7) Process for preparing benzoic acid derivatives (XIV) [the compounds of formula (I) in which $R^1$ is —OH, $R^2$ is a lower acyl group, and R is

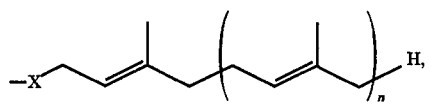

wherein X is an oxygen atom]:

Benzoic acid derivative (XIV) wherein $R^2$ is a lower acyl group can be obtained by reacting benzoic acid derivative (XIII) with an acid anhydride or acid halide in the presence of a base in accordance with the following reaction formula.

Any base can be used as long as no adverse influence is given to the reaction. Examples of suitable bases are pyridine and triethylamine.

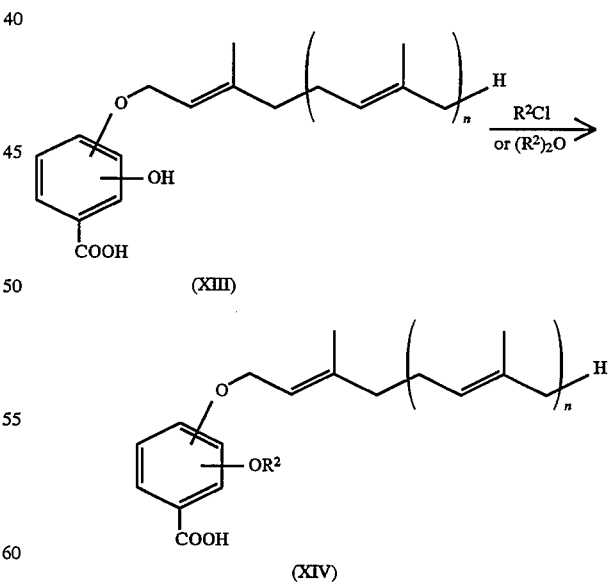
(XIII)

(XIV)

wherein n is as defined above; and $R^2$ represents a lower acyl group.

(8) Process for preparing benzoic acid derivatives (XV) [the compounds of formula (I) in which $R^1$ is —$NHR^3$; $R^2$ is a hydrogen atom; and R is

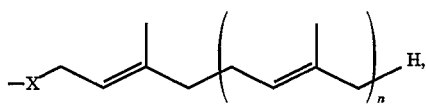

wherein X is an oxygen atom]:

Benzoic acid derivative (XIII) is treated with an acid halogenating agent, such as thionyl chloride, and then reacted with a primary amine in the presence of a base in accordance with the following reaction formula to obtain benzoic acid derivative (XV), the compound of formula (XIII) wherein $R^1$ is —$NHR^3$.

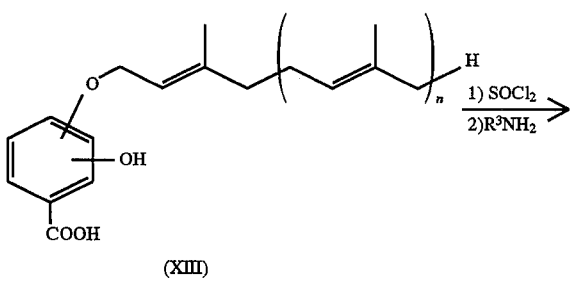

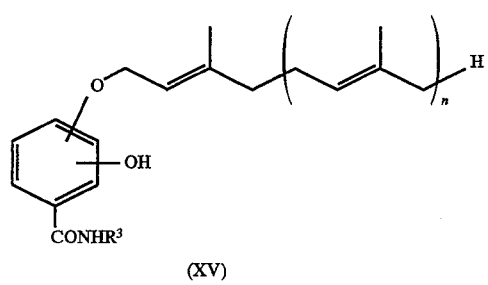

wherein n and $R^3$ are as defined above.

(9) Process for preparing benzoic acid derivatives (XVII) [the compounds of formula (I) in which $R^1$ is —OH, $R^2$ is a hydrogen atom; and R is

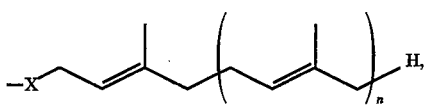

wherein X is —NH—]:

Benzoic acid derivative (XVII) can be obtained by reacting alkenyl halide (XI) with compound (XVI) in the presence or absence of a base in accordance with the following reaction formula.

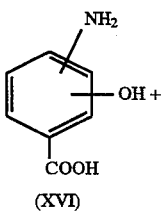

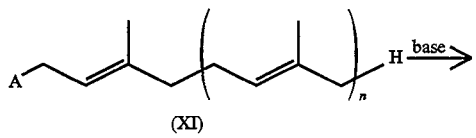

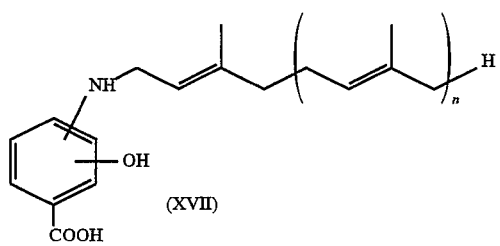

wherein n and A are as defined above.

The above reaction is preferably carried out by using 0.5 to 3.0 mol of compound (XI) per mole of compound (XVI) at a temperature of from −20° to 200° C., preferably 20° to 80° C., for several hours with stirring.

Any base can be used as long as no adverse influence is exerted on the reaction. Examples of suitable bases are sodium hydride, sodium amide, potassium carbonate, sodium carbonate, potassium hydroxide, and sodium hydroxide. Any solvent inert to the reaction can be used in the reaction. For example, N,N-dimethylformamide, dimethyl sulfoxide, tetrahydrofuran, ethanol or methanol is suitably used. After completion of the reaction, the solvent is removed by distillation, and the residue is purified by chromatography or a like means to isolate benzoic acid derivative (XVI).

The preparation for external application according to the present invention is not particularly restricted in form of use as far as it contains at least one of the benzoic acid derivatives represented by formula (I) and the benzoic acid derivative salts. The preparation is used as medicines for external use, medicinal cosmetics, cosmetics, and the like having a sebaceous secretion inhibitory effect due to the benzoic acid derivative or benzoic acid derivative salt. Other ingredients to be incorporated into the preparation are decided according to the form of use.

The medicines or medicinal cosmetics include various ointments containing a medical ingredient. The ointments may be either oily base-based ones or oil-in-water or water-in-oil emulsion-based ones. The oily base to be used is not particularly limited and includes vegetable oils, animal oils, synthetic oils, fatty acids, and natural or synthetic glycerides. The medical ingredient is not particularly limited. For example, analgesic antiinflammatory agents, analgesics, bactericidal disinfectants, astringents, emollients, hormones, vitamins, etc. can be used together with appropriately selected conventional components generally employed in pharmaceuticals and non-pharmaceuticals according to necessity.

For use as cosmetics, commonly employed cosmetic components, such as oily substances, humectants, ultraviolet absorbents, alcohols, chelating agents, pH adjusting agents, preservatives, thickeners, dyestuffs, and flavors, can be used in arbitrary combination.

The cosmetics include various forms to various purposes, for example, water-in-oil or oil-in-water emulsions, creams, milky lotions, clear lotions, oily cosmetics, facial packs, foundations, facial cleansings, hair tonics, shampoos, rinses, hair conditioners, hair restorers, and so on.

The above-mentioned preparations of various forms can easily be obtained in a conventional manner.

While not limiting, the amount of the benzoic acid derivative represented by formula (I) or the benzoic acid derivative salt in the preparation for external application to the skin according to the present invention usually ranges from 0.001 to 20% by weight (hereinafter simply referred to as %), preferably from 0.01 to 10%, based on the total preparation.

The benzoic acid derivatives in accordance with the present invention will be illustrated below in detail.

The benzoic acid derivatives of the present invention are benzoic acid derivatives represented by formula (II) (hereinafter referred to as benzoic acid derivatives A) and pharmacologically acceptable salts thereof.

In formula (II), the lower alkyl group and lower acyl group as represented by $R^6$ are the same as those represented by $R^2$ in formula (I). $R^7$ preferably includes a 2-ethylhexyl group, a 3,3,5-trimethylhexyl group, a cyclohexylmethyl group, a cyclohexylethyl group, and a 3,7-dimethyl-6-octenyl group.

The alkyl group and hydroxyalkyl group as represented by $R^8$ are the same as those represented by $R^3$ in formula (I).

The pharmacologically acceptable salt of benzoic acid derivative A (hereinafter referred to as a salt of benzoic acid derivative A) is a salt formed between benzoic acid derivative A and an arbitrary base.

Examples of the base include alkali metals, e.g., sodium and potassium; alkaline earth metals; ammonium; alkanolamines, e.g., triethanolamine; and basic amino acids, e.g., lysine and arginine.

Accordingly, the salts of benzoic acid derivative A include an alkali metal salt (e.g., a sodium salt or a potassium salt), an alkaline earth metal salt, an ammonium salt, an alkanolamine salt (e.g., a triethanolamine salt), and a basic amino acid salt (e.g., a lysine salt or an arginine salt) of benzoic acid derivative A.

The salt of benzoic acid derivative A is a salt formed by introducing the above-mentioned base into the position(s) (substituent(s)) of —$COR^5$ and/or —$OR^6$, preferably the position of —$COR^5$, in formula (II) wherein $R^5$ is —OH, and $R^6$ is a hydrogen atom.

The salt of benzoic acid derivative A can be prepared either by starting with a material previously converted into its salt in the processes hereinafter described or by introducing a salt forming step into the course of the processes described.

Specific examples of benzoic acid derivative A include methyl 4-(2-ethylhexyloxy)-2-hydroxybenzoate, methyl 2-hydroxy-4-(3,5,5-trimethylhexyloxy)benzoate, methyl 4-cyclohexylmethoxy-2-hydroxybenzoate, methyl 4-(2-cyclohexylethoxy)-2-hydroxybenzoate, methyl 4-(3,7-dimethyl-6-octenyloxy)-2-hydroxybenzoate, ethyl 3-(2-ethylhexyloxy)-5-hydroxybenzoate, methyl 5-(2-ethylhexyloxy)-2-hydroxybenzoate, methyl 2-hydroxy-5-(3,5,5-trimethylhexyloxy)benzoate, methyl 5-(2-cyclohexylethoxy)-2-hydroxybenzoate, 4-(2-ethylhexyloxy)-2-hydroxybenzoic acid, 2-hydroxy-4-(3,5,5-trimethylhexyloxy)benzoic acid, 4-cyclohexylmethoxy-2-hydroxybenzoic acid, 4-(2-cyclohexylethoxy)-2-hydroxybenzoic acid, 4-(3,7-dimethyl-6-octenyloxy)-2-hydroxybenzoic acid, 3-(2-ethylhexyloxy)-5-hydroxybenzoic acid, 5-(2-ethylhexyloxy)-2-hydroxybenzoic acid, 2-hydroxy-5-(3,5,5-trimethylhexyloxy)benzoic acid, 5-(2-cyclohexylethoxy)-2-hydroxybenzoic acid, N-(2-hydroxyethyl)-4-(2-ethylhexyloxy)-2-hydroxybenzamide, N-ethyl-4-(2-ethylhexyloxy)-2-hydroxybenzamide, 2-acetoxy-4-cyclohexylmethoxybenzoic acid, and sodium 4-(2-ethylhexyloxy)-2-hydroxybenzoate.

Benzoic acid derivatives A of the present invention can be obtained in the same manner as in processes (1) to (4) above described, except that $R^1$, $R^2$, $R^3$, and $R^4$ are replaced with $R^5$, $R^6$, $R^8$, and $R^7$, respectively.

Additionally, the benzoic acid derivatives according to the present invention are benzoic acid derivatives represented by formula (III) (hereinafter referred to as benzoic acid derivatives B).

In formula (III), the lower alkyl group and lower acyl group as represented by $R^{10}$ are the same as those represented by $R^2$ in formula (I). The alkyl group as represented by $R^{11}$ preferably includes lower alkyl groups having 1 to 5 carbon atoms, such as a methyl group, an ethyl group, a propyl group, an isopropyl group, a butyl group, and a pentyl group. The alkenyl group preferably includes those having 1 to 20 carbon atoms, such as a (2E)-3,7-dimethylocta-2,6-dienyl group and a (2E,6E)-3,7,11-trimethyl-2,6,10-dodecatrienyl group. The hydroxyalkyl group preferably includes lower hydroxyalkyl groups having 1 to 5 carbon atoms, such as a hydroxymethyl group, a 2-hydroxyethyl group, a 1-hydroxyethyl group, a 3-hydroxypropyl group, and a 5-hydroxypentyl group.

The pharmacologically acceptable salt of benzoic acid derivative B (hereinafter referred to as a salt of benzoic acid derivative B) is a salt formed between benzoic acid derivative B and an arbitrary base.

Examples of the base include alkali metals, e.g., sodium and potassium; alkaline earth metals; ammonium; alkanolamines, e.g., triethanolamine; and basic amino acids, e.g., lysine and arginine.

Accordingly, the salt of benzoic acid derivative B include an alkali metal salt (e.g., a sodium salt or a potassium salt), an alkaline earth metal salt, an ammonium salt, an alkanolamine salt (e.g., a triethanolamine salt), and a basic amino acid salt (e.g., a lysine salt or an arginine salt) of benzoic acid derivative B.

The salt of benzoic acid derivative B is a salt formed by introducing the above-mentioned base into the position(s) (substituent(s)) of —$COR^9$ and/or —$OR^{10}$, preferably the position of —$COR^9$, in formula (III) wherein $R^9$ is —OH, and $R^{10}$ is a hydrogen atom.

The salt of benzoic acid derivative B can be prepared either by starting with a material previously converted into its salt in the processes hereinafter described or by introducing a salt forming step into the course of the processes described.

Specific examples of benzoic acid derivative B preferably include methyl 4-{(2E)-3,7-dimethylocta-2,6-dienyloxy}-2-hydroxybenzoate, ethyl 4-{(2E)-3,7-dimethylocta-2,6-dienyloxy}-2-hydroxybenzoate, ethyl 5-{(2E)-3,7-dimethylocta-2,6-dienyloxy}-2-hydroxybenzoate, ethyl 3-{(2E)-3,7-dimethylocta-2,6-dienyloxy}-2-hydroxybenzoate, ethyl 3-{(2E)-3,7-dimethylocta-2,6-dienyloxy}-5-hydroxybenzoate, ethyl 4-{(2E)-3,7-dimethylocta-2,6-dienyloxy}-3-methoxybenzoate, methyl 4-{(2E,6E)-3,7,11-trimethyl-2,6,10-dodecatrienyloxy}-2-hydroxybenzoate, (2E)-3,7-dimethylocta-2,6-dienyl 4-{(2E)-3,7-dimethylocta-2,6-dienyloxy}-2-hydroxybenzoate, 4-{(2E)-3,7-dimethylocta-2,6-dienyloxy}-2-hydroxybenzoic acid, 5-{(2E)-3,7-dimethylocta-2,6-dienyloxy}-2-hydroxybenzoic acid, 3-{(2E)-3,7-dimethylocta-2,6-dienyloxy}-2-hydroxybenzoic acid, 3-{(2E)-3,7-dimethylocta-2,6-dienyloxy}-5-hydroxybenzoic acid, 2-hydroxy-4-{(2E,6E)-3,7,11-trimethyl-2,6,10-dodecatrienyl}benzoic acid, 4-{(2E)-3,7-dimethylocta-2,6-dienyloxy}-3-methoxybenzoic acid, 2-acetoxy-4-{(2E)-3,7-dimethylocta-2,6-dienyloxy}benzoic acid, N-(2-hydroxyethyl)-4-{(2E)-3,7-dimethylocta-2,6-dienyloxy}-2-hydroxybenzamide, and N-{(2E)-3,7-dimethylocta-2,6-dienyl}-4-amino-2-hydroxybenzoic acid.

Benzoic acid derivatives B of the present invention can be obtained in the same manner as in processes (5) to (9) above described, except that $R^1$, $R^2$, and $R^3$ are replaced with $R^9$, $R^{10}$, and $R^{11}$, respectively.

The benzoic acid derivatives according to the present invention, i.e., benzoic acid derivatives A, salts of benzoic acid derivatives A, benzoic acid derivatives B, and salts of benzoic acid derivatives B, have an sebaceous secretion inhibitory effect and are useful as a sebaceous secretion inhibiting agent. Also having action of suppressing or removing wrinkles, they are useful as an agent for wrinkle care. Additionally effective in prevention and reduction of pigmentation of melanin, they can be used as a melanin inhibitor.

EXAMPLES

The present invention will now be illustrated in greater detail with reference to Examples, but it should be understood that the present invention is not construed as being limited thereto. Examples 6 to 8, 12, 19 to 21, and 25 relate to synthesis of benzoic acid derivatives represented by formula (I); Examples 1 to 5, 9 to 11, 13 to 18, 22 to 24, and 26 to 30 relate to the benzoic acid derivatives represented by formula (II) (synthesis of the benzoic acid derivatives of formula (I)); Examples 31 to 47 relate to the benzoic acid derivatives represented by formula (III) (synthesis of the benzoic acid derivatives of formula (I); and Examples 48 to 57 relate to the preparations for external use according to the present invention.

EXAMPLE 1

Methyl 4-(2-Ethylhexyloxy)-2-hydroxybenzoate

To 30 ml of dimethylformamide (DMF) were added 5.00 g (29.9 mmol) of methyl 2,4-dihydroxybenzoate and 4.52 g (32.7 mmol) of potassium carbonate, and 6.32 g (32.7 mmol) of 2-ethylhexyl bromide was added thereto dropwise at room temperature. After the dropwise addition, the mixture was stirred at 80° C. for 5.5 hours. The reaction mixture was added to 200 ml of dilute hydrochloric acid and extracted with a 150 ml portion and two 50 ml portions of ethyl acetate. The resulting extract was washed successively with water and a saturated sodium chloride aqueous solution, dried over anhydrous sodium sulfate, and concentrated to obtain a crude product. The resultant crude product was purified by column chromatography to obtain 5.89 g (yield: 78%) of methyl 4-(2-ethylhexyloxy)-2-hydroxybenzoate represented by the following chemical formula (hereinafter referred to as compound 1) as a colorless, clear and oily substance. The analytical results of the product are shown below.

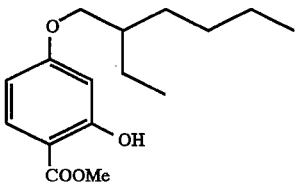

1

$^1$HNMR (CDCl$_3$, δ): 10.95 (s, 1H), 7.68–7.75 (m, 1H), 6.39–6.50 (m, 2H), 3.90 (s, 3H), 3.86 (d, 2H, J=5.8 Hz), 1.61–1.81 (m, 1H), 1.22–1.54 (m, 8H), 0.92 (t, 3H, J=7.3 Hz), 0.90 (t, 3H, J=5.7 Hz)

IR (neat, cm$^{-1}$): 3180, 2928, 2864, 1662, 1622, 1580, 1496, 1440, 1346, 1252, 1222, 1176, 1138, 1098, 1012, 964, 770

EXAMPLE 2

Methyl 2-Hydroxy-4-(3,5,5-trimethylhexyloxy)benzoate

Synthesis was carried out in the same manner as in Example 1, except for replacing 2-ethylhexyl bromide with 3,5,5-trimethylhexyl p-toluenesulfonate, to obtain methyl 2-hydroxy-4-(3,5,5-trimethylhexyloxy)benzoate represented by the following chemical formula (hereinafter referred to as compound 2) as a colorless, clear and oily substance in a yield of 52%. The analytical results are shown below.

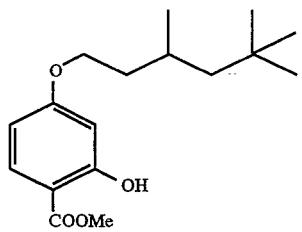

2

$^1$HNMR (CDCl$_3$, δ,ppm): 10.96 (s, 1H), 7.72 (d, 1H, J=9.5 Hz), 6.40–6.58 (m, 2H), 3.99 (t, 2H, J=6.4 Hz), 3.91 (s, 3H), 1.50–1.87 (m, 3H), 1.27 (dd, 1H, J=14.0, 3.2 Hz), 1.11 (dd, 1H, J=14.0, 5.6 Hz), 0.98 (d, 3H, J=6.4 Hz), 0.90 (s, 9H)

IR (neat, cm$^{-1}$): 3136, 2948, 2876, 1664, 1620, 1582, 1442, 1346, 1256, 1222, 1178, 1136

EXAMPLE 3

Methyl 4-Cyclohexylmethoxy-2-hydroxybenzoate

Synthesis was carried out in the same manner as in Example 1, except for replacing 2-ethylhexyl bromide with cyclohexylmethyl p-toluenesulfonate, to obtain methyl 4-cyclohexylmethoxy-2-hydroxybenzoate represented by the following chemical formula (hereinafter referred to as compound 3) as a white solid in a yield of 69%. The analytical results are shown below.

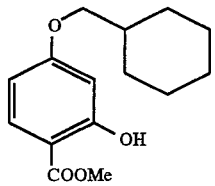

3

$^1$HNMR (CDCl$_3$, δ): 10.94 (s, 1H), 7.72 (d, 1H, J=9.5 Hz), 6.38–6.46 (m, 2H), 3.90 (s, 3H), 3.77 (d, 2H, J=6.1 Hz), 1.62–1.95 (m, 6H), 0.92–1.47 (m, 5H)

IR (KBr, cm$^{-1}$): 3092, 2920, 2848, 1658, 1620, 1580, 1498, 1438, 1250, 1220, 1182, 1134, 1094, 1008, 950, 770, 692

EXAMPLE 4

Methyl 4-(2-Cyclohexylethoxy)-2-hydroxybenzoate

Synthesis was carried out in the same manner as in Example 1, except for replacing 2-ethylhexyl bromide with 2-cyclohexylethyl p-toluenesulfonate, to obtain methyl 4-(2-cyclohexylmethoxy)-2-hydroxybenzoate represented by the following chemical formula (hereinafter referred to as compound 4) as a pale yellow solid in a yield of 91%. The analytical results are shown below.

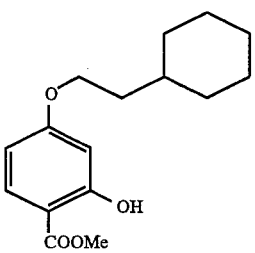

¹HNMR (CDCl₃, δ): 10.95 (s, 1H), 7.72 (d, 1H, J=9.5 Hz), 6.39–6.48 (m, 2H), 4.01 (t, 2H, J=6.6 Hz), 3.91 (s, 3H), 1.34–1.82 (m, 8H), 1.09–1.33 (m, 3H), 0.85–1.09 (m, 2H)

IR (KBr, cm⁻¹): 3180, 2928, 2848, 1664, 1614, 1576, 1472, 1440, 1336, 1252, 1182, 1132, 950, 772

EXAMPLE 5

Methyl 4-(3,7-Dimethyl-6-octenyloxy)-2-hydroxybenzoate

Synthesis was carried out in the same manner as in Example 1, except for replacing 2-ethylhexyl bromide with 3,7-dimethyl-6-octenyl chloride, to obtain methyl 4-(3,7-dimethyl-6-octenyloxy)-2-hydroxybenzoate represented by the following chemical formula (hereinafter referred to as compound 5) as a colorless, clear and oily substance in a yield of 28%. The analytical results are shown below.

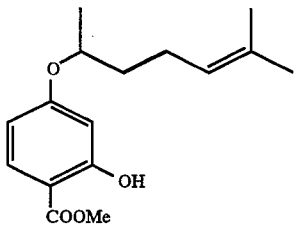

¹HNMR (CDCl₃, δ): 10.96 (s, 1H), 7.72 (d, 1H, J=9.5 Hz), 6.38–6.48 (m, 2H), 5.02–5.17 (m, 1H), 3.94–4.07 (m, 2H), 3.91 (s, 3H), 1.92–2.15 (m, 2H), 1.53–1.92 (m, 3H), 1.69 (s, 3H), 1.61 (s, 3H), 1.12–1.53 (m, 2H), 0.95 (d, 3H, J=6.3 Hz)

IR (neat, cm⁻¹): 3168, 3140, 3092, 2932, 1668, 1622, 1582, 1502, 1442, 1344, 1254, 1222, 1184, 1146, 1096, 1052, 1012, 966, 836, 770, 728, 696

EXAMPLE 6

Methyl 4-n-Hexyloxy-2-hydroxybenzoate

Synthesis was carried out in the same manner as in Example 1, except for replacing 2-ethylhexyl bromide with n-hexyl bromide, to obtain methyl 4-n-hexyloxy-2-hydroxybenzoate represented by the following chemical formula (hereinafter referred to as compound 6) as a white solid in a yield of 82%. The analytical results are shown below.

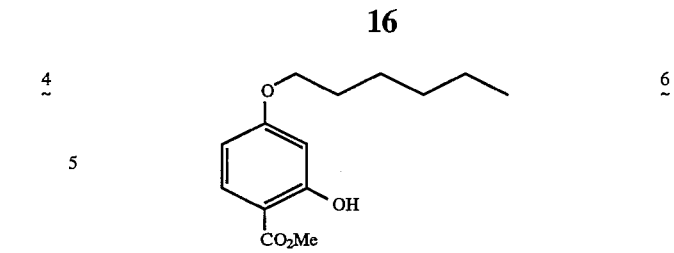

¹HNMR (CDCl₃, δ): 10.95 (s, 1H), 7.72 (d, 1H, J=9.4 Hz), 6.38–6.47 (m, 2H), 3.97 (t, 2H, J=6.5 Hz), 3.91 (s, 3H), 1.70–1.88 (m, 2H), 1.20–1.58 (m, 6H), 0.91 (t, 3H, J=6.5 Hz)

IR (KBr, cm⁻¹): 3188, 3060, 2936, 2856, 1658, 1614, 1580, 1498, 1442, 1342, 1256, 1122, 1018, 994, 946, 776

EXAMPLE 7

Methyl 2-Hydroxy-4-n-octyloxybenzoate

Synthesis was carried out in the same manner as in Example 1, except for replacing 2-ethylhexyl bromide with n-octyl bromide, to obtain methyl 2-hydroxy-4-n-octyloxybenzoate represented by the following chemical formula (hereinafter referred to as compound 7) as a colorless, clear and oily substance in a yield of 74%. The analytical results are shown below.

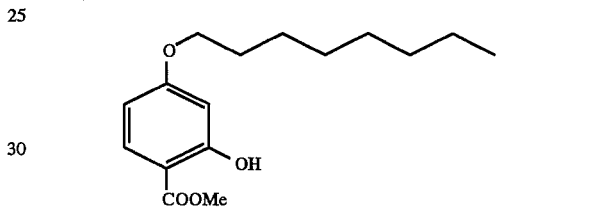

¹HNMR (CDCl₃, δ): 10.95 (s, 1H), 7.72 (d, 1H, J=9.5 Hz), 6.38–6.49 (m, 2H), 3.96 (t, 2H, J=6.5 Hz), 3.90 (s, 3H), 1.67–1.88 (m, 2H), 1.16–1.55 (m, 10H), 0.80–0.96 (m, 3H)

IR (neat, cm⁻¹): 3204, 2928, 2860, 1668, 1614, 1576, 1442, 1330, 1256, 1178, 1124, 1094, 858, 674

EXAMPLE 8

Methyl 4-n-Decyloxy-2-hydroxybenzoate

Synthesis was carried out in the same manner as in Example 1, except for replacing 2-ethylhexyl bromide with n-decyl bromide, to obtain methyl 4-n-decyloxy-2-hydroxybenzoate represented by the following chemical formula (hereinafter referred to as compound 8) as a white solid in a yield of 61%. The analytical results are shown below.

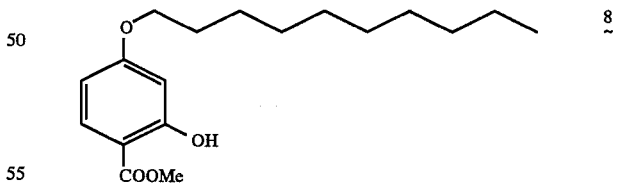

¹HNMR (CDCl₃, δ): 10.96 (s, 1H), 7.72 (d, 1H, J=9.5 Hz), 6.39–6.47 (m, 2H), 3.97 (t, 2H, J=6.5 Hz), 3.91 (s, 3H), 1.70–1.89 (m, 2H), 1.12–1.50 (m, 14H), 0.80–0.95 (m, 3H)

IR (KBr, cm⁻¹): 3208, 2924, 2852, 1668, 1614, 1576, 1444, 1330, 1248, 1178, 1124, 1090, 1046, 996, 972, 948, 772, 722, 696

EXAMPLE 9

Methyl 5-(2-Ethylhexyloxy)-2-hydroxybenzoate

Synthesis was carried out in the same manner as in Example 1, except for replacing methyl 2,4- dihydroxybenzoate with methyl 2,5-dihydroxybenzoate, to obtain methyl 5-(2-ethylhexyloxy)-2-hydroxybenzoate represented by the following chemical formula (hereinafter referred to as compound 9) as a colorless, clear and oily substance in a yield of 54%. The analytical results are shown below.

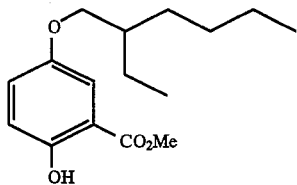

$^1$HNMR (CDCl$_3$, δ): 10.34 (s, 1H), 7.29 (d, 1H, J=3.1 Hz), 7.08 (dd, 1H, J=9.1, 3.1 Hz), 6.90 (d, 1H, J=9.1 Hz), 3.95 (s, 3H), 3.79 (d, 2H, J=5.6 Hz), 1.60–1.80 (m, 1H), 1.23–1.60 (m, 8H), 0.78–1.01 (m, 6H)

IR (neat, cm$^{-1}$): 3216, 2924, 2868, 1674, 1614, 1440, 1380, 1340, 1328, 1280, 1210, 1074, 1028, 784

EXAMPLE 10

Methyl 2-Hydroxy-5-(3,5,5-trimethylhexyloxy) benzoate

Synthesis was carried out in the same manner as in Example 1, except for replacing methyl 2,4-dihydroxybenzoate with methyl 2,5-dihydroxybenzoate and replacing 2-ethylhexyl bromide with 3,5,5-trimethylhexyl p-toluenesulfonate, to obtain methyl 5-(3,5,5-trimethylhexyloxy)-2-hydroxybenzoate represented by the following chemical formula (hereinafter referred to as compound 10) as a colorless, clear and oily substance in a yield of 76%. The analytical results are shown below.

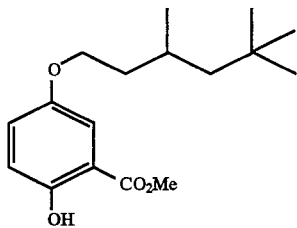

$^1$HNMR (CDCl$_3$, δ): 10.34 (s, 1H), 7.29 (d, 1H, J=3.1 Hz), 7.08 (dd, 1H, J=9.0, 3.1 Hz), 6.90 (d, 1H, J=9.0 Hz), 3.95 (s, 3H), 3.88–3.97 (m, 2H), 1.52–1.87 (m, 3H), 1.28 (dd, 1H, J=14.0, 3.4 Hz), 1.11 (dd, 1H, J=14.0, 5.7 Hz), 0.99 (d, 3H, J=6.5 Hz), 0.90 (s, 9H)

IR (neat, cm$^{-1}$): 3212, 2940, 1674, 1614, 1440, 1344, 1278, 1208, 1058

EXAMPLE 11

Methyl 5-(2-Cyclohexylethoxy)-2-hydroxybenzoate

Synthesis was carried out in the same manner as in Example 1, except for replacing methyl 2,4-dihydroxybenzoate with methyl 2,5-dihydroxybenzoate and replacing 2-ethylhexyl bromide with 2-cyclohexylethyl p-toluenesulfonate, to obtain methyl 5-(2-cyclohexylethoxy)-2-hydroxybenzoate represented by the following chemical formula (hereinafter referred to as compound 11) as a pale yellow solid in a yield of 43%. The analytical results are shown below.

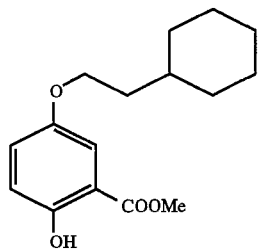

$^1$HNMR (CDCl$_3$, δ): 10.34 (s, 1H), 7.29 (d, 1H, J=3.1 Hz), 7.08 (dd, 1H, J=9.0, 3.1 Hz), 6.90 (d, 1H, J=9.0 Hz), 3.95 (s, 3H), 3.89–4.02 (m, 2H), 1.40–1.89 (m, 8H), 1.02–1.40 (m, 3H), 0.83–1.02 (m, 2H)

IR (KBr, cm$^{-1}$): 3228, 3136, 3060, 2916, 2856, 1662, 1614, 1586, 1436, 1386, 1324, 1272, 1186, 1078, 1030, 888, 784, 764, 662

EXAMPLE 12

Methyl 5-n-Hexyloxy-2-hydroxybenzoate

Synthesis was carried out in the same manner as in Example 1, except for replacing methyl 2,4-dihydroxybenzoate with methyl 2,5-dihydroxybenzoate and replacing 2-ethylhexyl bromide with n-hexyl bromide, to obtain methyl 5-n-hexyloxy-2-hydroxybenzoate represented by the following chemical formula (hereinafter referred to as compound 12) as a colorless, clear and oily substance in a yield of 58%. The analytical results are shown below.

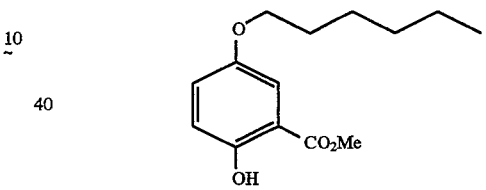

$^1$HNMR (CDCl$_3$, δ): 10.34 (s, 1H), 7.29 (d, 1H, J=3.0 Hz), 7.08 (dd, 1H, J=9.0, 3.0 Hz), 6.90 (d, 1H, J=9.0 Hz), 3.94 (s, 3H), 3.90 (t, 2H, J=6.5 Hz), 1.69–1.90 (m, 2H), 1.24–1.58 (m, 6H), 0.81–1.01 (m, 3H)

IR (neat, cm$^{-1}$): 3228, 2936, 2868, 1684, 1618, 1494, 1476, 1444, 1390, 1344, 1286, 1222, 1082, 1032, 978, 946, 900, 824, 786, 682

EXAMPLE 13

Ethyl 3-(2-Ethylhexyloxy)-5-hydroxybenzoate

Synthesis was carried out in the same manner as in Example 1, except for replacing methyl 2,4-dihydroxybenzoate with ethyl 3,5-dihydroxybenzoate, to obtain ethyl 3-(2-ethylhexyloxy)-5-hydroxybenzoate represented by the following chemical formula (hereinafter referred to as compound 13) as a colorless, clear and oily substance in a yield of 32%. The analytical results are shown below.

19

[Structure 13: 1,3-disubstituted benzene with HO, CO₂Et, and O-CH₂-CH(C₂H₅)-C₄H₉ (2-ethylhexyloxy) group]

$^1$HNMR (CDCl$_3$, δ): 7.11–7.17 (m, 2H), 6.61 (t, 1H, J=2.3 Hz), 5.49 (bs, 1H), 4.36 (q, 2H, J=7.1 Hz), 3.85 (d, 2H, J=5.7 Hz), 1.62–1.79 (m, 1H), 1.38 (t, 3H, J=7.1 Hz), 1.21–1.55 (m, 8H), 0.83–0.99 (m, 6H)

IR (neat, cm$^{-1}$): 3380, 2932, 2864, 1686, 1596, 1446, 1368, 1328, 1244, 1150, 1098, 1024, 764

EXAMPLE 14

4-(2-Ethylhexyloxy)-2-hydroxybenzoic Acid

In 100 ml of methanol was dissolved 6.44 g (23.1 mmol) of methyl 4-(2-ethylhexyloxy)-2-hydroxybenzoate (compound 1 obtained in Example 1), and an aqueous solution of 3.0 g (53.5 mmol) of KOH was added thereto at room temperature to obtain a reaction mixture. The resulting reaction mixture was heated under reflux for 4 hours, followed by cooling to room temperature, and methanol was evaporated. The residue was poured into 200 ml of dilute hydrochloric acid to be rendered acidic and then extracted with 200 ml of ethyl acetate. The extract was washed successively with two 200 ml portions of water and two 200 ml portions of a saturated sodium chloride aqueous solution, dried over anhydrous sodium sulfate, and concentrated. Recrystallization of the resulting crude product from ethyl acetate/hexane gave 4.64 g (76%) of 4-(2-ethylhexyloxy)-2-hydroxybenzoic acid represented by the following chemical formula (hereinafter referred to as compound 14) as white crystals. The analytical results of the product are shown below.

[Structure 14: 2-hydroxy-4-(2-ethylhexyloxy)benzoic acid with COOH and OH groups]

Melting Point (mp): 94.1°–96.5° C.

$^1$HNMR (CDCl$_3$, δ): 10.62 (s, 1H), 7.80 (d, 1H, J=9.0 Hz), 6.40–6.54 (m, 2H), 3.88 (d, 2H, J=5.7 Hz), 1.64–1.82 (m, 1H), 1.18–1.56 (m, 8H), 0.83–1.00 (m, 6H)

IR (KBr, cm$^{-1}$): 3300-2300 (b), 2956, 2932, 2860, 1622, 1574, 1502, 1426, 1374, 1344, 1184, 1146, 1096, 1016, 898, 838, 774

EXAMPLE 15

2-Hydroxy-4-(3,5,5-trimethylhexyloxy)benzoic Acid

Synthesis was carried out in the same manner as in Example 14, except for replacing compound 1 with compound 2, to obtain 2-hydroxy-4-(3,5,5-trimethylhexyloxy)benzoic acid represented by the following chemical formula (hereinafter referred to as compound 15) as white crystals in a yield of 72%. The analytical results are shown below.

20

[Structure 15: 2-hydroxy-4-(3,5,5-trimethylhexyloxy)benzoic acid]

mp: 120.9°–122.4° C.

$^1$HNMR (CDCl$_3$, δ): 10.62 (s, 1H), 7.81 (dd, 1H, J=8.2, 1.0 Hz), 6.40–6.55 (m, 2H), 4.01 (t, 2H, J=6.4 Hz), 1.50–1.91 (m, 3H), 1.27 (dd, 1H, J=14.0, 3.1 Hz), 1.12 (dd, 1H, J=14.0, 5.6 Hz), 0.99 (d, 3H, J=6.3 Hz), 0.90 (s, 9H)

IR (KBr, cm$^{-1}$): 3400-2300 (b), 2952, 2868, 2608, 2552, 1616, 1438, 1360, 1314, 1246, 1184, 1144, 1094, 1004, 972, 880, 838, 798, 770, 640

EXAMPLE 16

4-Cyclohexylmethoxy-2-hydroxybenzoic Acid

Synthesis was carried out in the same manner as in Example 14, except for replacing compound 1 with compound 3, to obtain 4-cyclohexylmethoxy-2-hydroxybenzoic acid represented by the following chemical formula (hereinafter referred to as compound 16) as white crystals in a yield of 81%. The analytical results are shown below.

[Structure 16: 4-cyclohexylmethoxy-2-hydroxybenzoic acid]

mp: 186.0°–187.2° C.

$^1$HNMR (CDCl$_3$, δ): 10.60 (s, 1H), 7.80 (d, 1H, J=8.7 Hz), 6.37–6.58 (m, 2H), 3.79 (d, 2H, J=6.0 Hz), 1.57–1.97 (m, 6H), 0.91–1.47 (m, 5H)

IR (KBr, cm$^{-1}$): 3300-2400 (b), 2976, 2928, 2852, 1644, 1616, 1442, 1360, 1292, 1242, 1192, 1144, 848, 774

EXAMPLE 17

4-(2-Cyclohexylethoxy)-2-hydroxybenzoic Acid

Synthesis was carried out in the same manner as in Example 14, except for replacing compound 1 with compound 4, to obtain 4-(2-cyclohexylethoxy)-2-hydroxybenzoic acid represented by the following chemical formula (hereinafter referred to as compound 17) as white crystals in a yield of 77%. The analytical results are shown below.

[Structure 17: 4-(2-cyclohexylethoxy)-2-hydroxybenzoic acid]

mp: 144.6°–145.3° C.

¹HNMR (CDCl₃, δ): 10.60 (s, 1H), 7.81 (d, 1H, J=8.7 Hz), 6.39–6.58 (m, 2H), 4.03 (t, 2H, J=6.7 Hz), 1.59–1.89 (m, 7H), 1.40–1.59 (m, 1H), 1.10–1.40 (m, 3H), 0.84–1.10 (m, 2H)

IR (KBr, cm⁻¹): 3300-2300, 2924, 2848, 1616, 1440, 1352, 1314, 1240, 1180, 1146, 1094, 976, 872, 822, 794, 774 3400-2400 (b), 2956, 2864, 1652, 1616, 1592, 1490, 1440, 1328, 1282, 1252, 1228, 1200, 826, 804, 764, 666

EXAMPLE 18

4-(3,7-Dimethyl-6-octenyloxy)-2-hydroxybenzoic Acid

Synthesis was carried out in the same manner as In Example 14, except for replacing compound 1 with compound 5, to obtain 4-(3,7-dimethyl-6-octenyloxy)-2-hydroxybenzoic acid represented by the following chemical formula (hereinafter referred to as compound 18) as white crystals in a yield of 42%. The analytical results are shown below.

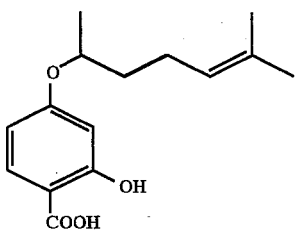

mp: 74°–82° C.

¹HNMR (CDCl₃, δ): 10.63 (s, 1H), 7.80 (d, 1H, J=9.2 Hz), 6.40–6.51 (m, 2H), 5.03–5.15 (m, 1H), 3.93–4.09 (m, 2H), 1.95–2.10 (m, 2H), 1.53–1.95 (m, 3H), 1.69 (s, 3H), 1.61 (s, 3H), 1.10–1.50 (m, 2H), 0.96 (d, 3H, J=6.3 Hz)

IR (KBr, cm⁻¹): 3300-2400 (b), 2932, 2860, 1624, 1452, 1432, 1380, 1248, 1146

EXAMPLE 19

4-n-Hexyloxy-2-hydroxybenzoic Acid

Synthesis was carried out in the same manner as in Example 14, except for replacing compound 1 with compound 6, to obtain 4-n-hexyloxy-2-hydroxybenzoic acid represented by the following chemical formula (hereinafter referred to as compound 19) as white crystals in a yield of 76%. The analytical results are shown below.

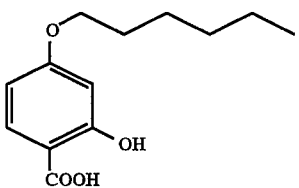

mp: 127.3°–128.5° C.

¹HNMR (CDCl₃, δ): 10.59 (s, 1H), 7.81 (d, 1H, J=8.9 Hz), 6.39–6.53 (m, 2H), 3.99 (t, 2H, J=6.6 Hz), 1.70–1.92 (m, 2H), 1.18–1.57 (m, 6H), 0.80–1.02 (m, 3H)

IR (KBr, cm⁻¹): 3300-2300 (b), 2936, 2856, 1622, 1500, 1430, 1384, 1352, 1324, 1240, 1188, 1148, 1092, 1010, 960, 896, 844

EXAMPLE 20

2-Hydroxy-4-n-octyloxybenzoic Acid

Synthesis was carried out in the same manner as in Example 14, except for replacing compound 1 with compound 7, to obtain 2-hydroxy-4-n-octyloxybenzoic acid represented by the following chemical formula (hereinafter referred to as compound 20) as white crystals in a yield of 62%. The analytical results are shown below.

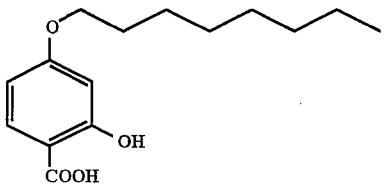

mp: 104.4°–105.7° C.

¹HNMR (CDCl₃, δ): 10.60 (s, 1H), 7.81 (d, 1H, J=8.8 Hz), 6.38–6.52 (m, 2H), 3.99 (t, 2H, J=6.5 Hz), 1.72–1.86 (m, 2H), 1.18–1.56 (m, 10H), 0.80–1.03 (m, 3H)

IR (KBr, cm⁻¹): 3300-2400 (b), 2928, 2856, 1662, 1620, 1574, 1498, 1454, 1436, 1388, 1350, 1246, 1196, 1148, 1094, 1068, 858, 674, 644

EXAMPLE 21

4-n-Decyloxy-2-hydroxybenzoic Acid

Synthesis was carried out in the same manner as in Example 14, except for replacing compound 1 with compound 8, to obtain 4-n-decyloxy-2-hydroxybenzoic acid represented by the following chemical formula (hereinafter referred to as compound 21) as white crystals in a yield of 83%. The analytical results are shown below.

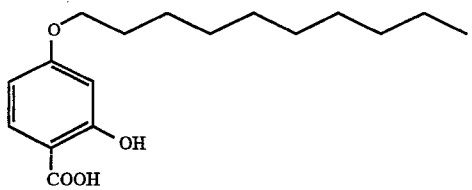

mp: 100.5°–102.4° C.

¹HNMR (CDCl₃, δ): 10.01 (bs, 1H), 7.81 (d, 1H, J=8.8 Hz), 6.42–6.51 (m, 2H), 3.99 (t, 2H, J=6.5 Hz), 1.71–1.89 (m, 2H), 1.10–1.56 (m, 14H), 0.72–1.02 (m, 3H)

IR (KBr, cm⁻¹): 3300-2300 (b), 2928, 2852, 1616, 1442, 1358, 1318, 1234, 1178, 1146, 1090, 1012, 966, 890, 840, 776

EXAMPLE 22

5-(2-Ethylhexyloxy)-2-hydroxybenzoic Acid

Synthesis was carried out in the same manner as in Example 14, except for replacing compound 1 with compound 9, to obtain 5-(2-ethylhexyloxy)-2-hydroxybenzoic acid represented by the following chemical formula (hereinafter referred to as compound 22) as white crystals in a yield of 58%. The analytical results are shown below.

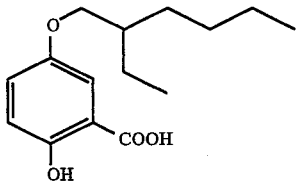

mp: 82.6°–84.3° C.

¹HNMR (CDCl₃, δ): 10.01 (s, 1H), 7.36 (d, 1H, J=3.1 Hz), 7.16 (dd, 1H, J=9.0, 3.1 Hz), 6.93 (d, 1H, J=9.0 Hz), 5.69 (d, 2H, J=5.7 Hz), 1.60–1.81 (m, 1H), 1.19–1.60 (m, 8H), 0.82–1.04 (m, 6H)

IR (KBr, cm$^{-1}$): 3400–2400 (b), 2956, 2864, 1652, 1616, 1592, 1490, 1440, 1328, 1282, 1252, 1228, 1200, 826, 804, 764, 666

EXAMPLE 23

2-Hydroxy-5-(3,5,5-trimethylhexyloxy)benzoic Acid

Synthesis was carried out in the same manner as in Example 14, except for replacing compound 1 with compound 10, to obtain 2-hydroxy-5-(3,5,5-trimethylhexyloxy) benzoic acid represented by the following chemical formula (hereinafter referred to as compound 23) as white crystals in a yield of 47%. The analytical results are shown below.

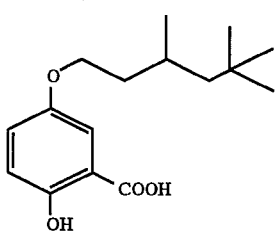

mp: 92.2°–93.8° C.

$^1$HNMR (CDCl$_3$, δ): 10.02 (s, 1H), 7.36 (d, 1H, J=3.1 Hz), 7.15 (dd, 1H, J=9.1, 3.1 Hz), 6.94 (d, 1H, J=9.1 Hz), 3.95 (t, 2H, J=6.4 Hz), 1.48–1.89 (m, 3H), 1.29 (dd, 1H, J=14.0, 3.3 Hz), 1.12 (dd, 1H, J=14.0, 5.7 Hz), 0.99 (d, 3H, J=6.3 Hz), 0.91 (s, 3H)

IR (KBr, cm$^{-1}$): 3500–2450 (b), 2956, 2908, 2880, 1644, 1594, 1442, 1386, 1366, 1328, 1250, 1228, 1198, 1080, 1022, 858, 828, 802, 766, 662

EXAMPLE 24

5-(2-Cyclohexylethoxy)-2-hydroxybenzoic Acid

Synthesis was carried out in the same manner as in Example 14, except for replacing compound 1 with compound 11, to obtain 5-(2-cyclohexylethoxy)-2-hydroxybenzoic acid represented by the following chemical formula (hereinafter referred to as compound 24) as white crystals in a yield of 60%. The analytical results are shown below.

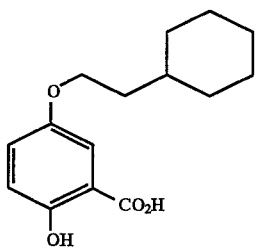

mp: 145.2°–146.5° C.

$^1$HNMR (CDCl$_3$, δ): 10.02 (s, 1H), 7.35 (d, 1H, J=3.1 Hz), 7.15 (dd, 1H, J=9.1, 3.1 Hz), 6.94 (d, 1H, J=9.1 Hz), 3.97 (t, 2H, J=6.6 Hz), 0.85–1.84 (m, 13 Hz)

IR (KBr, cm$^{-1}$): 3400–2350 (b), 2914, 2852, 1648, 1614, 1592, 1438, 1396, 1330, 1278, 1228, 1022, 880, 830, 806, 762, 668

EXAMPLE 25

5-n-Hexyloxy-2-hydroxybenzoic Acid

Synthesis was carried out in the same manner as in Example 14, except for replacing compound 1 with compound 12, to obtain 5-n-hexyloxy-2-hydroxybenzoic acid represented by the following chemical formula (hereinafter referred to as compound 25) as white crystals in a yield of 40%. The analytical results are shown below.

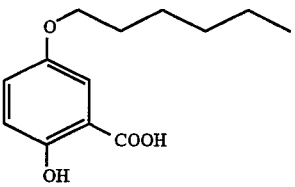

mp: 86.3°–89.5° C.

$^1$HNMR (CDCl$_3$, δ): 10.00 (s, 1H), 7.36 (d, 1H, J=3.1 Hz), 7.15 (dd, 1H, J=9.0, 3.1 Hz), 6.94 (d, 1H, J=9.0 Hz), 3.93 (t, 3H, J=6.5 Hz), 1.68–1.89 (m, 2H), 1.21–1.59 (m, 6H), 0.82–1.05 (m, 3H)

IR (KBr, cm$^{-1}$): 3500–2400 (b), 2964, 2932, 2860, 1660, 1620, 1596, 1494, 1450, 1394, 1334, 1288, 1258, 1230, 1204, 962, 830, 798, 776, 686

EXAMPLE 26

3-(2-Ethylhexyloxy)-5-hydroxybenzoic Acid

Synthesis was carried out in the same manner as in Example 14, except for replacing compound 1 with compound 13, to obtain 3-(2-ethylhexyloxy)-5-hydroxybenzoic acid represented by the following chemical formula (hereinafter referred to as compound 26) as white crystals in a yield of 73%. The analytical results are shown below.

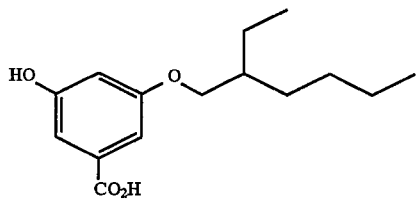

mp: 113.6°–116.1° C.

$^1$HNMR (DMSO-d$_6$, δ): 12.76 (bs, 1H), 9.67 (bs, 1H), 6.94 (s, 1H), 6.90 (s, 1H), 6.52 (s, 1H), 3.72–3.95 (m, 2H), 1.55–1.79 (m, 1H), 1.15–1.55 (m, 8H), 0.70–1.10 (m, 6H)

IR (KBr, cm$^{-1}$): 3600–2500 (b), 2928, 2864, 1714, 1602, 1444, 1392, 1326, 1296, 1236, 1204, 1152, 1034, 770, 712, 642

EXAMPLE 27

N-(2-Hydroxyethyl)-4-(2-ethylhexyloxy)-2-hydroxybenzamide

In 10 ml of methylene chloride was dissolved 0.40 g (1.5 mmol) of 4-(2-ethylhexyloxy)-2-hydroxybenzoic acid (compound 14), and a small amount of DMF was added thereto. To the solution was added dropwise 0.14 ml (2.0 mmol) of thionyl chloride, followed by stirring at room temperature for 45 minutes. The solvent was removed by distillation under reduced pressure, and 10 ml of methylene chloride was added to the residue. To the solution was added dropwise 5 ml of a 20 wt % solution of 2-ethanolamine in methylene chloride. The solvent was removed by distillation under reduced pressure, and 50 ml of dilute hydrochloric acid was added thereto, followed by extraction with 50 ml of ethyl acetate. The ethyl acetate layer was washed successively with two 50 ml portions of water and a 50 ml portion of a saturated sodium chloride aqueous solution, dried over anhydrous sodium sulfate, and concentrated to obtain a crude product. The crude product was subjected to column chromatography to obtain 0.12 g (26%) of N-(2-hydroxyethyl)-4-(2-ethylhexyl)-2-hydroxybenzamide represented by the following chemical formula (hereinafter referred to as compound 27) as a colorless, clear, and oily substance. The analytical results are shown below.

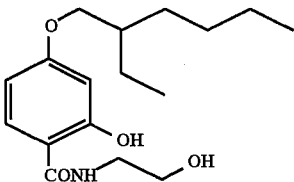

$^1$HNMR (CDCl$_3$, δ): 12.51 (bs, 1H), 7.27 (d, 1H, J=8.7 Hz), 6.56 (bs, 1H), 6.45 (d, 1H, J=2.5 Hz), 6.40 (dd, 1H, J=8.7, 2.5 Hz), 3.78–3.90 (m, 4H), 3.57–3.67 (m, 2H), 2.18 (bs, 1H), 1.18–1.80 (m, 9H), 0.80–1.02 (m, 6H)

IR (neat, cm$^{-1}$): 3700-2300 (b), 3380, 2924, 1600, 1584, 1504, 1462, 1362, 1260, 1160, 1110, 1026, 794

EXAMPLE 28

N-Ethyl-4-(2-ethylhexyloxy)-2-hydroxybenzamide

In 30 ml of pyridine was dissolved 3.00 g (11.3 mmol) of 4-(2-ethylhexyloxy)-2-hydroxybenzoic acid (compound 14), and 2.89 g (28.4 mmol) of acetic anhydride was added to the solution dropwise on an ice-water bath. After the dropwise addition, the mixture was stirred for 20 minutes, poured into 120 ml of a 12% aqueous solution of hydrochloric acid, and extracted with 150 ml of ethyl acetate. The organic layer was washed successively with three 150 ml portions of dilute hydrochloric acid, three 150 ml portions of water, and three 100 ml portions of a saturated aqueous solution of sodium chloride, and dried over anhydrous sodium sulfate, followed by concentration. The resulting crude product was dissolved in 10 ml of methylene chloride, and a few drops of DMF were added thereto. To the mixture was further added dropwise 1.57 g (13.2 mmol) of methylene chloride at room temperature, followed by stirring for 15 minutes. The solvent was removed by distillation under reduced pressure, and the oily residue was dissolved in methylene chloride. The solution was added to 10 ml of a 70% aqueous solution of ethylamine on an ice bath. After the inner temperature was raised to room temperature, 300 ml of dilute hydrochloric acid was added thereto, and the mixture was extracted with 300 ml of ethyl acetate. The organic layer was washed successively with three 300 ml portions of water and two 300 ml portions of a saturated sodium chloride aqueous solution, dried over anhydrous sodium sulfate, and concentrated. The resulting crude product was recrystallized from hexane to obtain 2.06 g (62%) of N-ethyl-4-(2-ethylhexyloxy)-2-hydroxybenzamide represented by the following chemical formula (hereinafter referred to as compound 28) as white crystals. The analytical results are shown below.

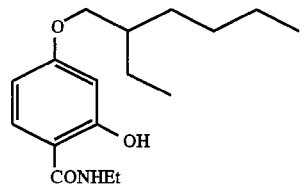

mp: 48.5°–50.8° C.

$^1$HNMR (CDCl$_3$, δ): 12.71 (s, 1H), 7.22 (d, 1H, J=8.8 Hz), 6.45 (d, 1H, J=2.4 Hz), 6.39 (dd, 1H, J=8.8, 2.4 Hz), 6.06 (bs, 1H), 3.84 (d, 2H, J=5.6 Hz), 3.47 (qd, 2H, J=7.2, 5.6 Hz), 1.62–1.70 (m, 1H), 1.26 (t, 3H, J=7.2 Hz), 1.21–1.53 (m, 8H), 0.83–1.04 (m, 6H)

IR (KBr, cm$^{-1}$): 3384, 2960, 2932, 2872, 1592, 1504, 1460, 1376, 1336, 1256, 1188, 1160, 808

EXAMPLE 29

2-Acetoxy-4-cyclohexylmethoxybenzoic Acid

In 2 ml of pyridine was dissolved 0.30 g (1.2 mmol) of 4-cyclohexylmethyl-2-hydroxybenzoic acid (compound 16), and 0.30 g (3.0 mmol) of acetic anhydride was added dropwise to the solution at room temperature, followed by stirring for 20 minutes. The reaction mixture was poured into 10 ml of a 12% aqueous solution of hydrochloric acid and extracted with two 50 ml portions of ethyl acetate. The extract was washed successively with three 50 ml portions of dilute hydrochloric acid, three 50 ml portions of water, and two 50 ml portions of a saturated aqueous solution of sodium chloride, and dried over anhydrous sodium sulfate, followed by concentration. Recrystallization of the resulting crude product from hexane afforded 0.17 g (yield: 48%) of 2-acetoxy-4-cyclohexylmethoxybenzoic acid represented by the following chemical formula (hereinafter referred to as compound 29) as white crystals. The analytical results are shown below.

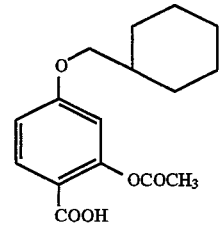

mp: 116.1°–117.9° C.

$^1$HNMR (CDCl$_3$, δ): 8.05 (d, 1H, J=8.9 Hz), 6.82 (dd, 1H, J=8.9, 2.5 Hz), 6.61 (d, 1H, J=2.5 Hz), 3.80 (d, 2H, J=6.0 Hz), 2.34 (s, 3H), 1.65–1.96 (m, 6H), 0.85–1.48 (m, 5H)

IR (KBr, cm$^{-1}$): 3400, 2500 (b), 2924, 2856, 1762, 1686, 1608, 1416, 1364, 1330, 1272, 1244, 1206, 1170, 1148, 1082

EXAMPLE 30

Sodium 4-(2-Ethylhexyloxy)-2-hydroxybenzoate

In 15 ml of ethanol was dissolved 1.24 g (4.7 mmol) of 4-(2-ethyloxy)-2-hydroxybenzoic acid (compound 14), and 0.94 ml (4.7 mmol) of a 5 mol/l NaOH aqueous solution was added thereto. The solvent was evaporated, ethanol added to the residue, and the mixture azeotropically dehydrated. The residue was dried by heating to obtain sodium 4-(2-ethylhexyloxy)-2-hydroxybenzoate represented by the following chemical formula (hereinafter referred to as compound 30).

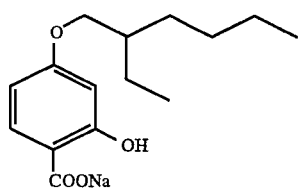

¹HNMR (DMSO-d₆, δ): 11.88 (s, 1H), 7.59 (d, 1H, J=9.2 Hz), 6.00–6.23 (m, 2H), 3.78 (d, 2H, J=5.6 Hz), 1.52–1.73 (m, 1H), 1.20–1.52 (m, 8H), 0.72–0.98 (m, 6H)

IR (KBr, cm⁻¹): 3384, 3324, 3220, 2960, 2868, 1644, 1574, 1512, 1444, 1372, 1260, 1148, 1090, 780, 674, 606, 576

EXAMPLE 31

In 80 m of DMF were poured 13.1 g (78.0 mmol) of methyl 2,4-dihydroxybenzoate and 18.9 g (86.9 mmol) of potassium carbonate, and 12.0 g (86.9 mmol) of geranyl bromide was added thereto dropwise at 5° C. After the addition, the mixture was stirred at room temperature for 1 hour, poured into 300 ml of water, and extracted with 250 ml of ethyl acetate. The extract was washed with water and a saturated sodium chloride aqueous solution, dried over sodium sulfate, and concentrated. The resulting crude product was purified by column chromatography to obtain 18.1 g (yield: 75%) of methyl 4-{(2E)-3,7-dimethylocta-2,6-dienyloxy}-2-hydroxybenzoate represented by the following chemical formula (hereinafter referred to as compound 31) as a colorless, clear and oily substance. The analytical results are shown below.

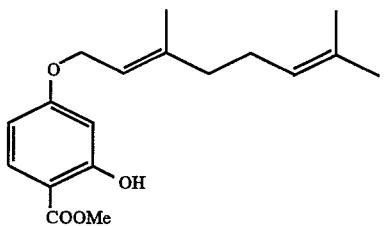

¹HNMR (CDCl₃, δ, ppm): 10.95 (s, 1H), 7.73 (d, 1H, J=9.5 Hz), 6.40–6.47 (m, 2H), 5.40–5.52 (m, 1H), 5.04–5.19 (m, 1H), 4.55 (d, 2H, J=6.5 Hz), 3.91 (s, 3H), 1.95–2.21 (m, 4H), 1.73 (s, 3H), 1.68 (s, 3H), 1.60 (s, 3H)

IR (neat, cm⁻¹): 3140, 2916, 2860, 1668, 1662, 1582, 1502, 1440, 1380, 1348, 1254, 1222, 1184, 1140, 1096, 998, 774

EXAMPLE 32

Synthesis was carried out in the same manner as in Example 31, except for starting with ethyl 2,4-dihydroxybenzoate, to obtain ethyl 4-{(2E)-3,7-dimethylocta-2,6-dienyloxy}-2-hydroxybenzoate represented by the following chemical formula (hereinafter referred to as compound 32) as a colorless, clear and oily substance in a yield of 73%. The analytical results are shown below.

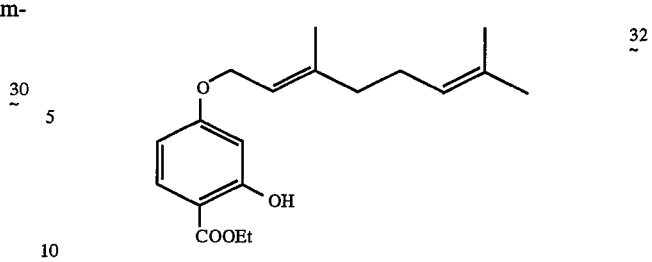

¹HNMR (CDCl₃, δ, ppm): 11.04 (s, 1H), 7.74 (d, 1H, J=9.6 Hz), 6.39–6.49 (m, 2H), 5.41–5.52 (m, 1H), 5.02–5.15 (m, 1H), 4.55 (d, 2H, J=6.5 Hz), 4.37 (q, 2H, J=7.1 Hz), 2.10 (s, 4H), 1.74 (s, 3H), 1.68 (s, 3H), 1.61 (s, 3H), 1.39 (t, 3H, J=7.1 Hz)

IR (neat, cm⁻¹): 3140, 2976, 2920, 2864, 1658, 1624, 1582, 1462, 1372, 1336, 1252, 1220, 1170, 1146, 1092, 996

EXAMPLE 33

Synthesis was carried out in the same manner as in Example 31, except for starting with ethyl 2,5-dihydroxybenzoate, to obtain ethyl 5-{(2E)-3,7-dimethylocta-2,6-dienyloxy}-2-hydroxybenzoate represented by the following chemical formula (hereinafter referred to as compound 33) as a colorless, clear and oily substance in a yield of 64%. The analytical results are shown below.

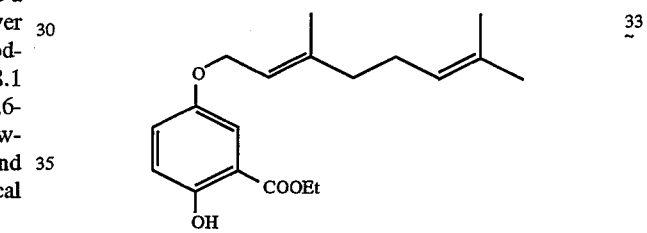

¹HNMR (CDCl₃, δ, ppm): 10.43 (s, 1H), 7.33 (d, 1H, J=3.1 Hz), 7.09 (dd, 1H, J=9.0, 3.1 Hz), 6.90 (d, 1H, J=9.0 Hz), 5.40–5.54 (m, 1H), 5.01–5.15 (m, 1H), 4.50 (d, 2H, J=6.6 Hz), 4.40 (q, 2H, J=7.1 Hz), 2.09 (s, 4H), 1.74 (s, 3H), 1.67 (s, 3H), 1.60 (s, 3H), 1.41 (t, 3H, J=7.1 Hz)

IR (neat, cm⁻¹): 3250, 2976, 2924, 1720, 1672, 1614, 1486, 1404, 1376, 1322, 1280, 1210, 1076, 1004, 818, 788, 680

EXAMPLE 34

Synthesis was carried out in the same manner as in Example 31, except for starting with ethyl 2,3-dihydroxybenzoate, to obtain ethyl 3-{(2E)-3,7-dimethylocta-2,6-dienyloxy}-2-hydroxybenzoate represented by the following structural formula (hereinafter referred to as compound 34) as a colorless, clear and oily substance in a yield of 22%. The analytical results are shown below.

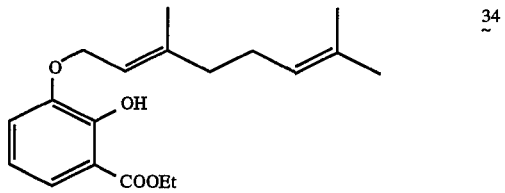

¹HNMR (CDCl₃, δ, ppm): 11.08 (s, 1H), 7.56 (d, 1H, J=8.0 Hz), 7.05 (d, 1H, J=8.0 Hz), 6.79 (dd, 1H, J=8.0, 8.0

Hz), 5.44–5.61 (m, 1H), 5.01–5.15 (m, 1H), 4.64 (d, 2H, J=6.5 Hz), 4.34 (q, 2H, J=7.1 Hz), 2.08 (s, 4H), 1.73 (s, 3H), 1.67 (s, 3H), 1.60 (s, 3H), 1.41 (t, 3H, J=7.1 Hz)

IR (neat, cm$^{-1}$): 3128, 2968, 2916, 1670, 1616, 1586, 1456, 1374, 1318, 1294, 1242, 1164, 1088, 1032, 746

EXAMPLE 35

Synthesis was carried out in the same manner as in Example 31, except for starting with ethyl 3,5-dihydroxybenzoate, to obtain ethyl 3-{(2E)-3,7-dimethylocta-2,6-dienyloxy}-5-hydroxybenzoate represented by the following structural formula (hereinafter referred to as compound 35) as a colorless, clear and oily substance in a yield of 30%. The analytical results are shown below.

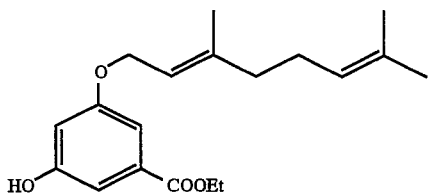

$^1$HNMR (CDCl$_3$, δ, ppm): 7.05–7.21 (m, 2H), 6.59–6.66 (m, 1H), 5.38–5.53 (m, 1H), 5.15 (s, 1H), 5.02–5.14 (m, 1H), 4.54 (d, 2H, J=6.5 Hz), 4.34 (q, 2H, J=7.1 Hz), 2.10 (s, 4H), 1.74 (s, 3H), 1.67 (s, 3H), 1.59 (s, 3H), 1.37 (t, 3H, J=7.1 Hz)

IR (neat, cm$^{-1}$): 3392, 2972, 2916, 1720, 1688, 1598, 1494, 1448, 1372, 1346, 1318, 1250, 1152, 1100, 1024, 766

EXAMPLE 36

Synthesis was carried out in the same manner as in Example 31, except for starting with ethyl 4-hydroxy-3-methoxybenzoate, to obtain ethyl 4-{(2E)-3,7-dimethylocta-2,6-dienyloxy}-3-methoxybenzoate represented by the following structural formula (hereinafter referred to as compound 36) as a colorless, clear and oily substance in a yield of 82%. The analytical results are shown below.

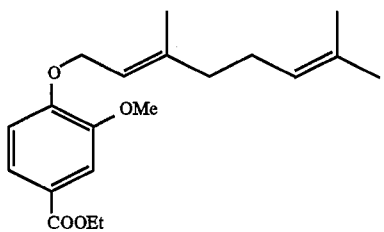

$^1$HNMR (CDCl$_3$, δ, ppm): 7.6 (dd, 1H, J=8.4, 1.9 Hz), 7.55 (d, 1H, J=1.9 Hz), 6.88 (d, 1H, J=8.4 Hz), 5.50 (t, 1H, J=6.5 Hz), 5.00–5.12 (m, 1H), 4.68 (d, 2H, J=6.5 Hz), 4.36 (q, 2H, J=7.1 Hz), 3.92 (s, 3H), 2.08 (s, 4H), 1.74 (s, 3H), 1.67 (s, 3H), 1.60 (s, 3H), 1.39 (t, 3H, J=7.1 Hz)

IR (neat, cm$^{-1}$): 2972, 2916, 2860, 1708, 1596, 1506, 1456, 1416, 1368, 1344, 1284, 1214, 1178, 1130, 1102, 1022, 994, 926, 872, 760

EXAMPLE 37

In 10 m of DMF were poured 1.28 g (7.6 mmol) of methyl 2,4-dihydroxybenzoate and 1.05 g (7.6 mmol) of potassium carbonate, and 1.84 g (7.6 mmol) of farnesyl chloride was added thereto dropwise at room temperature. After the addition, the mixture was stirred at 60° C. for 3 hours and then poured into a 12% hydrochloric acid aqueous solution. Ethyl acetate was poured thereinto to conduct extraction. The resulting extract was washed with water and a saturated sodium chloride aqueous solution, dried over sodium sulfate, and concentrated. The resulting crude product was purified by column chromatography on silica gel to obtain 2.0 g (yield: 71%) of methyl 4-{(2E,6E)-3,7,11-trimethyl-2,6,10-dodecatrienyloxy}-2-hydroxybenzoate represeted by the following structural formula (hereinafter referred to as compound 37) as a colorless, clear and oily substance. The analytical results are shown below.

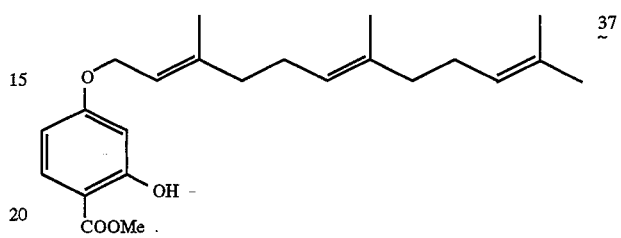

$^1$HNMR (CDCl$_3$, δ, ppm): 10.96 (s, 1H), 7.72 (d, 1H, J=9.5 Hz), 6.38–6.50 (m, 2H), 5.40–5.52 (m, 1H), 4.98–5.15 (m, 2H), 4.55 (d, 2H, J=6.6 Hz), 3.91 (s, 3H), 1.85–2.21 (m, 8H), 1.74 (s, 3H), 1.68 (s, 3H), 1.60 (s, 6H)

IR (neat, cm$^{-1}$): 3192, 2920, 2860, 1666, 1622, 1582, 1500, 1442, 1382, 1344, 1252, 1222, 1186, 1140, 1098, 996, 772

EXAMPLE 38

In 100 m of DMF were poured 10.0 g (64.9 mmol) of 2,4-dihydroxybenzoic acid and 22.4 g (162 mmol) of potassium carbonate, and 35.2 g (162 mmol) of geranyl bromide was added thereto dropwise at room temperature. After the addition, the mixture was stirred at room temperature for 1 hour and then poured into 300 ml of water. Hexane was poured thereinto to conduct extraction. The resulting extract was washed with water and a saturated sodium chloride aqueous solution, dried over sodium sulfate, and concentrated. The resulting crude product was purified by column chromatography on silica gel to obtain 23.8 g (yield: 86%) of (2E)-3,7-dimethylocta-2,6-dienyl 4-{(2E)-3,7-dimethylocta-2,6-dienyloxy}-2-hydroxybenzoate represented by the following structural formula (hereinafter referred to as compound 38) as a colorless, clear and oily substance. The analytical results are shown below.

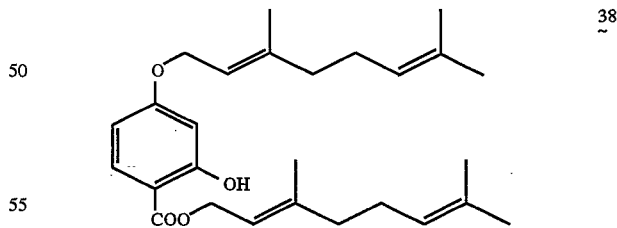

$^1$HNMR (CDCl$_3$, δ, ppm): 11.06 (s, 1H), 7.75 (d, 1H, J=9.4 Hz), 6.39–6.51 (m, 2H), 5.40–5.54 (m, 2H), 5.00–5.18 (m, 2H), 4.83 (d, 2H, J=7.1 Hz), 4.55 (d, 2H, J=6.6 Hz), 2.10 (s, 8H), 1.75 (s, 3H), 1.74 (s, 3H), 1.68 (s, 6H), 1.61 (s, 6H)

IR (neat, cm$^{-1}$): 3124, 3100, 2964, 2924, 1722, 1662, 1622, 1582, 1500, 1444, 1382, 1352, 1248, 1220, 1174, 1138, 1088, 998, 772

EXAMPLE 39

In methanol was dissolved 18.1 g (59.5 mmol) of methyl 4-{(2E)-3,7-dimethylocta-2,6-dienyloxy}-2- hydroxybenzoate, and 30 ml of an aqueous solution of 8.35 g (148 mmol) of potassium hydroxide was added thereto, followed by heating under reflux for 5 hours. Methanol was evaporated, and a 12% hydrochloric acid aqueous solution added to the residue, followed by extraction with ethyl acetate. The organic layer was washed successively with water and a saturated aqueous solution of sodium chloride and dried over sodium sulfate, followed by concentration. The resulting crude product was recrystallized from an ethyl acetate/hexane mixed solvent to obtain 13.06 g (yield: 75%) of 4-{(2E)-3,7-dimethylocta-2,6-dienyloxy}-2-hydroxybenzoic acid represented by the following structural formula (hereinafter referred to as compound 39) as white crystals. The analytical results are shown below.

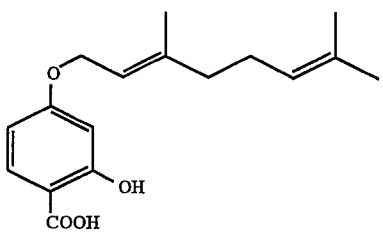

mp: 101.3°–102.4° C.

$^1$HNMR (DMSO-$d_6$, δ, ppm): 13.5 (bs), 11.53 (bs, 1H), 7.68 (d, 1H, J=9.5 Hz), 6.42–6.53 (m, 2H), 5.41 (t, 1H, J=6.5 Hz), 5.00–5.14 (m, 1H), 4.59 (d, 2H, J=6.5 Hz), 2.05 (s, 4H), 1.71 (s, 3H), 1.62 (s, 3H), 1.56 (s, 3H)

IR (KBr, cm$^{-1}$): 3200-2500, 1620, 1492, 1456, 1384, 1354, 1314, 1240, 1188, 1144, 1092, 996, 972, 912, 846, 778, 694, 638

EXAMPLE 40

Synthesis was carried out in the same manner as in Example 39, except for starting with ethyl 5-{(2E)-3,7-dimethylocta-2,6-dienyloxy}-2-hydroxybenzoate, to obtain 5-{(2E)-3,7-dimethylocta-2,6-dienyloxy}-2-hydroxybenzoic acid represented by the following structural formula (hereinafter referred to as compound 40) as white crystals in a yield of 69%. The analytical results are shown below.

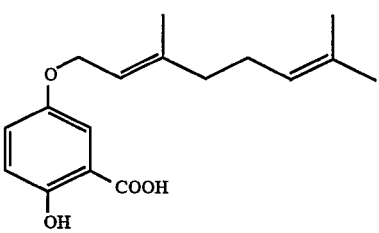

mp: 90.6°–92.9° C.

$^1$HNMR (DMSO-$d_6$, δ, ppm): 14.2 (bs), 11.92 (bs, 1H), 7.26 (d, 1H, J=3.1 Hz), 7.14 (dd, 1H, J=9.0, 3.1 Hz), 6.88 (d, 1H, J=9.0 Hz), 5.37 (t, 1H, J=6.4 Hz), 4.96–5.12 (m, 1H), 4.51 (d, 2H, J=6.4 Hz), 2.03 (s, 4H), 1.70 (s, 3H), 1.61 (s, 3H), 1.56 (s, 3H)

IR (KBr, cm$^{-1}$): 3300-2500, 2964, 2916, 2856, 1646, 1614, 1588, 1486, 1440, 1376, 1332, 1296, 1240, 1224, 1004, 856, 836, 786, 768

EXAMPLE 41

Synthesis was carried out in the same manner as in Example 39, except for starting with ethyl 3-{(2E)-3,7-dimethylocta-2,6-dienyloxy}-2-hydroxybenzoate, to obtain 3-{(2E)-3,7-dimethylocta-2,6-dienyloxy}-2-hydroxybenzoic acid represented by the following structural formula (hereinafter referred to as compound 41) as white crystals in a yield of 61%. The analytical results are shown below.

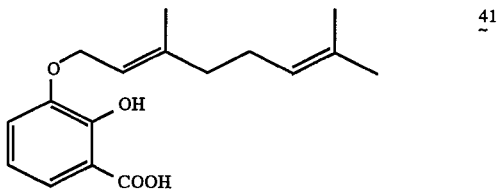

mp: 91.1°–94.7° C.

$^1$HNMR (DMSO-$d_6$, δ, ppm): 13.95 (bs), 11.51 (bs, 1H), 7.35 (d, 1H, J=8.0 Hz), 7.20 (d, 1H, J=8.0 Hz), 6.82 (dd, 1H, J=8.0, 8.0 Hz), 5.36–5.51 (m, 1H), 4.99–5.51 (m, 1H), 4.57 (d, 2H, J=6.6 Hz), 2.05 (s, 4H), 1.69 (s, 3H), 1.63 (s, 3H), 1.59 (s, 3H)

IR (KBr, cm$^{-1}$): 3200-2500, 1660, 1468, 1384, 1306, 1248, 1236, 1012, 902, 744

EXAMPLE 42

Synthesis was carried out in the same manner as in Example 39, except for starting with ethyl 3-{(2E)-3,7-dimethylocta-2,6-dienyloxy}-5-hydroxybenzoate, to obtain 3-{(2E)-3,7-dimethylocta-2,6-dienyloxy}-5-hydroxybenzoic acid represented by the following structural formula (hereinafter referred to as compound 42) as white crystals in a yield of 75%. The analytical results are shown below.

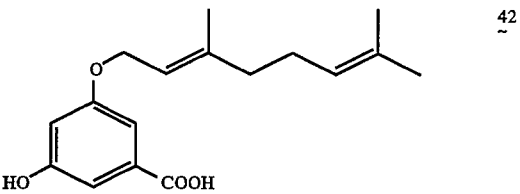

mp: 113.1°–114.2° C.

$^1$HNMR (DMSO-$d_6$, δ, ppm): 12.80 (bs), 9.72 (bs, 1H), 6.94 (d, 1H, J=2.2 Hz), 6.91 (d, 1H, J=2.2 Hz), 6.53 (dd, 1H, J=2.2, 2.2 Hz), 5.38 (t, 1H, J=6.3 Hz), 4.90–5.11 (m, 1H), 4.53 (d, 2H, J=6.3 Hz), 2.04 (s, 4H), 1.70 (s, 3H), 1.62 (s, 3H), 1.56 (s, 3H)

IR (KBr, cm$^{-1}$): 3500-2500, 2968, 2920, 2856, 1720, 1606, 1504, 1448, 1382, 1346, 1306, 1246, 1218, 1152, 1040, 984, 798, 712

EXAMPLE 43

Synthesis was carried out in the same manner as in Example 39, except for starting with methyl 4-{(2E,6E)-3,7,11-trimethyl-2,6,10-dodecatrienyloxy}-2-hydroxybenzoate, to obtain 2-hydroxy-4-{(2E,6E)-3,7,11-trimethyl-2,6,10-dodecatrienyloxy}benzoic acid represented by the following structural formula (hereinafter referred to as compound 43) as white crystals in a yield of 62%. The analytical results are shown below.

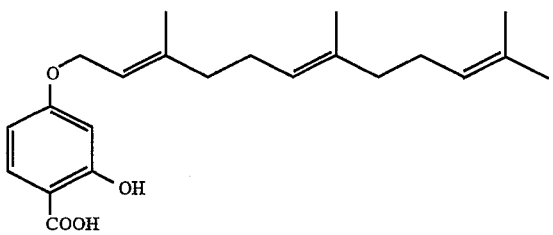

43 mp: 86.5°–87.3° C.

¹HNMR (DMSO-d₆, δ, ppm): 13.90 (bs), 11.59 (bs, 1H), 7.68 (d, 1H, J=9.5 Hz), 6.42–6.53 (m, 2H), 5.40 (t, 1H, J=6.5 Hz), 4.95–5.14 (m, 2H), 4.59 (d, 2H, J=6.5 Hz), 1.82–2.21 (m, 8H), 1.71 (s, 3H), 1.63 (s, 3H), 1.56 (s, 3H), 1.55 (s, 3H)

IR (KBr, cm⁻¹): 3300-2400, 1624, 1580, 1454, 1384, 1354, 1312, 1244, 1192, 1140, 1094, 970, 906, 842, 780

EXAMPLE 44

Synthesis was carried out in the same manner as in Example 39, except for starting with ethyl 4-{(2E)-3,7-dimethylocta-2,6-dienyloxy}-3-methoxybenzoate, to obtain 4-{(2E)-3,7-dimethylocta-2,6-dienyloxy}-3-methoxybenzoic acid represented by the following structural formula (hereinafter referred to as compound 44) as white crystals in a yield of 83%. The analytical results are shown below.

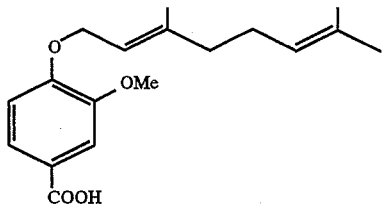

44 mp: 93.2°–94.1° C.

¹HNMR (DMSO-d₆, δ, ppm): 12.6 (bs, 1H), 7.54 (dd, 1H, J=8.4, 1.9 Hz), 7.44 (d, 1H, J=1.9 Hz), 7.02 (d, 1H, J=8.4 Hz), 5.43 (t, 1H, J=6.4 Hz), 4.98–5.12 (m, 1H), 4.61 (d, 2H, J=6.4 Hz), 3.80 (s, 3H), 2.06 (s, 4H), 1.71 (s, 3H), 1.63 (s, 3H), 1.57 (s, 3H)

IR (KBr, cm⁻¹): 3140, 2916, 2860, 1668, 1662, 1582, 1502, 1440, 1380, 1348, 1254, 1222, 1184, 1140, 1096, 998, 774

EXAMPLE 45

To 10 ml of a pyridine solution containing 0.82 g (2.82 mmol) of 4-{(2E)-3,7-dimethylocta-2,6-dienyloxy}-2-hydroxybenzoic acid was added 0.72 g (7.1 mmol) of acetic anhydride, followed by stirring at room temperature for 1 hour. The reaction mixture was poured into a 2% hydrochloric acid aqueous solution and extracted with ethyl acetate. The organic layer was washed successively with water and a saturated sodium chloride aqueous solution, dried over sodium sulfate, and concentrated. The resulting crude product was recrystallized from an ethyl ether/hexane mixed solvent to obtain 0.45 g (yield: 48%) of 2-acetoxy-4-{(2E)-3,7-dimethylocta-2,6-dienyloxy}benzoic acid represented by the following structural formula (hereinafter referred to as compound 45) as white crystals. The analytical results are shown below.

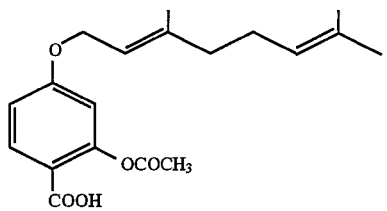

45 mp: 88.3°–91.6° C.

¹HNMR (DMSO-d₆, δ, ppm): 12.71 (bs, 1H), 7.87 (d, 1H, J=8.8 Hz), 6.91 (dd, 1H, J=8.8, 2.5 Hz), 6.76 (d, 1H, J=2.5 Hz), 5.39–5.50 (m, 1H), 5.00–5.12 (m, 1H), 4.62 (d, 2H, J=6.5 Hz), 2.22 (s, 3H), 2.05 (s, 4H), 1.71 (m, 3H), 1.63 (s, 3H), 1.57 (s, 3H)

IR (KBr, cm⁻¹): 3200-2500, 2968, 2916, 1762, 1678, 1608, 1568, 1418, 1372, 1278, 1242, 1204, 1172, 1152, 1090, 1012, 896

EXAMPLE 46

In 50 ml of n-octane was dissolved 2.00 g (6.9 mmol) of 4-{(2E)-3,7-dimethylocta-2,6-dienyloxy}-2-hydroxybenzoic acid, and 5.0 ml (35 mmol) of thionyl chloride was added to the solution, followed by heating at 90° C. for 5 hours to conduct a reaction. After completion of the reaction, the reaction mixture was cooled, and n-octane was removed by evaporation. The residue was dissolved in n-octane, and a pyridine solution of 0.84 g (13.8 mmol) of 2-hydroxyethylamine was added thereto dropwise at room temperature. After the dropwise addition, the mixture was stirred for 10 minutes, poured into a 12% hydrochloric acid aqueous solution, and extracted with ethyl acetate. The organic layer was washed with water and then with a saturated sodium chloride aqueous solution, dried over sodium sulfate, and concentrated. The resulting crude product was recrystallized from an ethyl acetate/hexane mixed solvent to obtain 0.50 g (yield: 22%) of N-(2-hydroxyethyl)-4-{(2E)-3,7-dimethylocta-2,6-dienyloxy}-2-hydroxybenzamide represented by the following structural formula (hereinafter referred to as compound 46) as white crystals. The analytical results are shown below.

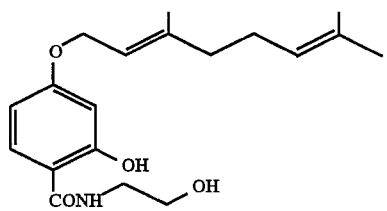

46 mp: 66.3°–67.5° C.

¹HNMR (CDCl₃, δ, ppm): 12.53 (bs, 1H), 7.21–7.34 (m, 1H), 6.61–6.78 (m, 1H), 6.34–6.51 (m, 2H), 5.46 (t, 1H, J=6.5 Hz), 5.01–5.15 (m, 1H), 4.54 (d, 2H, J=6.5 Hz), 3.83 (t, 2H, J=5.0 Hz), 3.60 (dt, 2H, J=5.0, 5.0 Hz), 2.32 (bs, 1H), 2.10 (s, 4H), 1.73 (s, 3H), 1.68 (s, 3H), 1.60 (s, 3H)

IR (KBr, cm⁻¹): 3408, 2964, 2912, 2856, 1642, 1592, 1508, 1416, 1378, 1260, 1192, 1160

EXAMPLE 47

In 30 ml of DMF was dissolved 2.12 g (13.8 mmol) of 4-amino-2-hydroxybenzoic acid, and 3.0 g (13.8 mmol) of geranyl bromide was added thereto. After the mixture was stirred at room temperature for 4 hours, water was added thereto, and the mixture was extracted with ethyl acetate.

The organic layer was washed with water and a saturated sodium chloride aqueous solution, dried over anhydrous sodium sulfate, and concentrated. The resulting crude product was purified by column chromatography and recrystallized from ethyl acetate/hexane to obtain 0.30 g (yield: 7.6%) of N-{(2E)-3,7-dimethylocta-2,6-dienyl}-4-amino-2-hydroxybenzoic acid represented by the following structural formula (hereinafter referred to as compound 47) as white crystals. The analytical results are shown below.

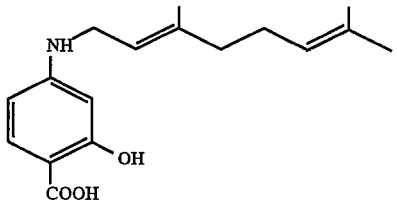

mp: 117.3°–119.1° C.

$^1$HNMR (CDCl$_3$, δ, ppm): 10.71 (s, 1H), 7.67 (d, 1H, J=8.7 Hz), 6.06–6.14 (m, 2H), 5.27–5.33 (m, 1H), 5.06–5.09 (m, 1H), 3.74 (d, 2H, J=6.6 Hz), 2.07 (s, 4H), 1.71 (s, 3H), 1.69 (s, 3H), 1.61 (s, 3H)

IR (KBr, cm$^{-1}$): 3396, 2916, 1620, 1536, 1440, 1394, 1258, 1226, 1160, 1088

EXAMPLE 48

A clear lotion having the following composition was prepared in a conventional manner.
Clear Lotion (Composition; wt %):

| | |
|---|---|
| Glycerin | 5.0 |
| Propylene glycol | 4.0 |
| Oleyl alcohol | 0.1 |
| Polyoxyethylene sorbitan monolaurate (20E.O.) | 1.5 |
| Polyoxyethylene lauryl ether (20E.O.) | 0.5 |
| Ethanol | 8.5 |
| Compound 1 | 1.0 |
| Purified water | the balance |

EXAMPLE 49

A facial pack having the following composition was prepared in a conventional manner.
Facial Pack (Composition: wt %):

| | |
|---|---|
| Polyvinyl alcohol | 15.0 |
| Sodium carboxymethyl cellulose | 5.0 |
| Propylene glycol | 3.0 |
| Compound 11 | 0.5 |
| Ethanol | 12.0 |
| Purified water | the balance |

EXAMPLE 50

An emollient cream having the following composition was prepared in a conventional manner.
Emollient Cream (Composition: wt %):

| | |
|---|---|
| Stearic acid | 14.0 |
| Vaseline | 2.0 |
| Self-emulsifiable glycerol monostearate | 2.5 |
| Polyoxyethylene sorbitan monostearate (20E.O.) | 0.2 |
| Propylene glycol | 10.0 |

-continued

| | |
|---|---|
| Compound 16 | 7.0 |
| Purified water | the balance |

EXAMPLE 51

A hair tonic having the following composition was prepared in a conventional manner.
Hair Tonic (Composition; wt %):

| | |
|---|---|
| dl-α-Tocopherol acetate | 0.2 |
| Swertia extract | 0.1 |
| Hinokitiol | 0.1 |
| Compound 21 | 3.5 |
| β-Glycyrrhetinic acid | 0.5 |
| 1-Menthol | 0.5 |
| Dipropylene glycol | 3.0 |
| Ethanol | 65.0 |
| Purified water | the balance |

EXAMPLE 52

A shampoo having the following composition was prepared in a conventional manner.
Shampoo (Composition; wt %):

| | |
|---|---|
| Sodium alkylsulfate | 16.0 |
| Lauric acid diethanolamide | 4.0 |
| Propylene glycol | 2.0 |
| Compound 24 | 2.5 |
| Purified water | the balance |

EXAMPLE 53

A clear lotion having the following composition was prepared in a conventional manner.
Clear Lotion (Composition; wt %):

| | |
|---|---|
| Glycerin | 5.0 |
| Propylene glycol | 4.0 |
| Oleyl alcohol | 0.1 |
| Polyoxyethylene sorbitan monolaurate (20E.O.) | 1.5 |
| Polyoxyethylene lauryl ether (20E.O.) | 0.5 |
| Compound 31 | 1.0 |
| Ethanol | 10.0 |
| Purified water | the balance |

EXAMPLE 54

A facial pack having the following composition was prepared in a conventional manner.
Facial Pack (Composition: wt %):

| | |
|---|---|
| Polyvinyl alcohol | 15.0 |
| Sodium carboxymethyl cellulose | 5.0 |
| Propylene glycol | 3.0 |
| Compound 32 | 0.5 |
| Ethanol | 10.0 |
| Purified water | the balance |

EXAMPLE 55

An emollient cream having the following composition was prepared in a conventional manner.

Emollient Cream (Composition: wt %):

| | |
|---|---|
| Compound 33 | 10.0 |
| Stearic acid | 14.0 |
| Vaseline | 2.0 |
| Self-emulsifiable glycerol monostearate | 2.5 |
| Polyoxyethylene sorbitan monostearate (20E.O.) | 0.2 |
| Propylene glycol | 10.0 |
| Purified water | the balance |

EXAMPLE 56

A hair tonic having the following composition was prepared in a conventional manner.

Hair Tonic (Composition; wt %):

| | |
|---|---|
| dl-α-Tocopherol acetate | 0.2 |
| Swertia extract | 0.1 |
| Hinokitiol | 0.1 |
| Compound 39 | 3.5 |
| β-Glycyrrhetinic acid | 0.5 |
| l-Menthol | 0.5 |
| Dipropylene glycol | 3.0 |
| Ethanol | 60.0 |
| Purified water | the balance |

EXAMPLE 57

A shampoo having the following composition was prepared in a conventional manner.

Shampoo (Composition; wt %):

| | |
|---|---|
| Compound 46 | 5.0 |
| Sodium alkylsulfate | 16.0 |
| Lauric acid diethanolamide | 4.0 |
| Propylene glycol | 2.0 |
| Purified water | the balance |

TEST EXAMPLE

The following test was conducted to evaluate the sebum synthesis inhibitory action of the benzoic acid derivatives according to the present invention.

Measurement of sebum synthesis was made in accordance with the method of Hall, et al. (cf. Arch. Dermatol. Res., 275:1–7 (1983)). The skin tissue (diameter: 4 mm) containing sebaceous glands, taken from the auricle of a male hamster, was cultured in a Krebes-Ringer's phosphate-buffered solution containing radioactive sodium acetate for 3 hours. The tissue was hydrolyzed and extracted with hexane. The amount of the radioactive labelled lipids in the hexane fraction was measured with a liquid scintillation counter to obtain the amount of the synthesized sebum. The skin tissue obtained from the left auricle of a hamster was tested using a Krebes-Ringer's phosphate-buffered solution, while that obtained from the right one of the same hamster was tested using a Krebes-Ringer's phosphate-buffered solution containing each of the compounds shown in Tables 1 and 2, and a percent synthesis inhibition was obtained according to the following numerical formula. The results obtained are shown in Tables 1 and 2. The percent sebum synthesis inhibition of each compound is an average of 6 animals.

Percent sebum synthesis inhibition (%) =
100 − (amount of sebum synthesized in the presence of a test compound)/(amount of sebum synthesized in the absence of a test compound) × 100

TABLE 1

| Compound No. | Concentration (μM) | Percent Sebum Synthesis Inhibition (%) |
|---|---|---|
| 1 | 100 | 32 |
| 14 | 10 | 60 |
| 15 | 10 | 66 |
| 16 | 10 | 44 |
| 17 | 10 | 57 |
| 18 | 10 | 45 |
| 19 | 8 | 58 |
| 20 | 8 | 26 |
| 21 | 8 | 13 |
| 22 | 8 | 84 |
| 23 | 8 | 83 |
| 24 | 8 | 78 |
| 25 | 8 | 80 |
| 27 | 8 | 15 |
| 29 | 8 | 48 |

TABLE 2

| Compound No. | Concentration (μM) | Percent Sebum Synthesis Inhibition (%) |
|---|---|---|
| 39 | 100 | 93 |
| 39 | 10 | 52 |
| 40 | 10 | 72 |
| 41 | 100 | 91 |
| 42 | 100 | 70 |
| 43 | 100 | 47 |
| 45 | 100 | 47 |
| 46 | 10 | 28 |

POSSIBLE INDUSTRIAL UTILITY

The preparation for external application to the skin according to the present invention has a sufficient sebaceous secretion inhibitory effect with no side effect and is of high safety for human body. Therefore, the preparation is effective to improve the skin conditions or diseases accompanying excessive sebaceous secretion, such as acne and scurf (corresponding to claim 1).

The benzoic acid derivatives represented by formula (II) according to the present invention are novel compounds. They have an sebaceous secretion inhibitory effect and the like and can be utilized as an active ingredient of sebaceous secretion inhibitory preparations, etc. (corresponding to claim 2).

The benzoic acid derivatives represented by formula (III) according to the present invention are novel compounds. They have sufficient sebaceous secretion inhibitory activity with no substantial side effect and high safety for human body (corresponding to claim 3).

What is claimed is:

1. A preparation for external application to the skin which comprises at least one of benzoic acid derivatives represented by formula (I):

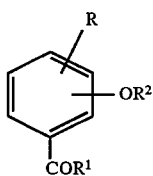

wherein R¹ represents —OH, —OR³ or —NHR³; R² represents a hydrogen atom, a lower alkyl group or a lower acyl group; R represents —O—R⁴ or

R³ represents an alkyl group, an alkenyl group or a hydroxyalkyl group; R⁴ represents a straight-chain or branched, saturated or unsaturated alkyl group or cycloalkylalkyl group having from 4 to 10 carbon atoms; X represents —O— or —NH—; and n represents 1 or 2, or a pharmacologically acceptable salt thereof as an active ingredient and an acceptable carrier for the skin.

2. The preparation for external application according to claim 1, wherein said benzoic acid derivative is a compound of the formula:

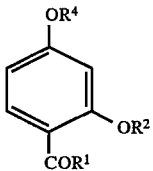

wherein R¹ represents —OH, —OR³ or —NHR³; R² represents a hydrogen atom, a lower alkyl group or a lower acyl group; R³ represents an alkyl group, an alkenyl group or a hydroxyalkyl group; and R⁴ represents a straight-chain or branched, saturated or unsaturated alkyl group or cycloalkylalkyl group having from 4 to 10 carbon atoms.

3. The preparation for external application according to claim 1, wherein said benzoic acid derivative is a compound of the formula:

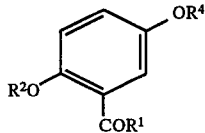

wherein R¹ represents —OH, —OR³ or —NHR³; R² represents a hydrogen atom, a lower alkyl group or a lower acyl group; R³ represents an alkyl group, an alkenyl group or a hydroxyalkyl group; and R⁴ represents a straight-chain or branched, saturated or unsaturated alkyl group or cycloalkylalkyl group having from 4 to 10 carbon atoms.

4. A method of inhibiting sebaceous secretion which comprises applying an effective sebaceous inhibiting amount of a composition according to claim 1, to the skin of a user.

5. The preparation for external application to the skin, according to claim 1, wherein said benzoic acid derivative is at least one selected from the group consisting of methyl 4-(2-ethylhexyloxy)-2-hydroxybenzoate, methyl 2-hydroxy-4-(3,5,5-trimethylhexyloxy)benzoate, methyl-4-cyclohexylmethoxy-2-hydroxybenzoate, methyl 4-(2-cyclohexylethoxy)-2-hydroxybenzoate, methyl 4-(3,7-dimethyl-6-octenyloxy)-2- hydroxybenzoate, ethyl 3-(2-ethylhexyloxy)-5-hydroxybenzoate, methyl 5-(2-ethylhexyloxy)-2-hydroxybenzoate, methyl 2-hydroxy-5-(3,5,5-trimethylhexyloxy)benzoate, methyl 5-(2-cyclohexylethoxy)-2-hydroxybenzoate, methyl 4-n-hexyloxy-2-hydroxybenzoate, methyl 2-hydroxy-4-n-octyloxybenzoate, methyl 4-n-decyloxy-2-hydroxybenzoate, methyl 5-n-hexyloxy-2-hydroxybenzoate, 4-(2-ethylhexyloxy)-2-hydroxybenzoic acid, 2-hydroxy-4-(3,5,5-trimethylhexyloxy)benzoic acid, 4-cyclohexylmethoxy-2-hydroxybenzoic acid, 4-(2-cyclohexylethoxy)-2-hydroxybenzoic acid, 4-(3,7-dimethyl-6-octenyloxy)-2-hydroxybenzoic acid, 3-(2-ethylhexyloxy)-5-hydroxybenzoic acid, 5-(2-ethylhexyloxy)-2-hydroxybenzoic acid, 2-hydroxy-5-(3,5,5-trimethylhexyloxy)benzoic acid, 5-(2-cyclohexylethoxy)-2-hydroxybenzoic acid, 4-n-hexyloxy-2-hydroxybenzoic acid, 5-n-hexyloxy-2-hydroxybenzoic acid, 2-hydroxy-4-n-octyloxybenzoic acid, 4-n-decyloxy-2-hydroxybenzoic acid, N-(2-hydroxyethyl)-4-(2-ethylhexyloxy)-2-hydroxybenzamide, N-ethyl-4-(2-ethylhexyloxy)-2-hydroxybenzamide, 2-acetoxy-4-cyclohexylmethoxybenzoic acid, sodium 4-(2-ethylhexyloxy)-2-hydroxybenzoate, methyl 4-{(2E)-3,7-dimethylocta-2,6-dienyloxy}-2-hydroxybenzoate, ethyl 4-{(2E)-3,7-dimethylocta-2,6-dienyloxy}-2-hydroxybenzoate, ethyl 5-{(2E)-3,7-dimethylocta-2,6-dienyloxy}-2-hydroxybenzoate, ethyl 3-{(2E)-3,7-dimethylocta-2,6-dienyloxy}-2-hydroxybenzoate, ethyl 3-{(2E)-3,7-dimethylocta-2,6-dienyloxy}-5-hydroxybenzoate, ethyl 4-{(2E)-3,7-dimethylocta-2,6-dienyloxy}-3-methoxybenzoate, methyl 4-{(2E,6E)-3,7,11-trimethyl-2,6,10-dodecatrienyl}-2 -hydroxybenzoate, (2E)-3,7-dimethylocta-2,6-dienyl 4-{(2E)-3,7-dimethylocta-2,6-dienyloxy}-2-hydroxybenzoate, 4-{(2E)-3,7-dimethylocta-2,6-dienyloxy}-2-hydroxybenzoic acid, 5-{(2E)-3,7-dimethylocta-2,6-dienyloxy}-2-hydroxybenzoic acid, 3-{(2E)-3,7-dimethylocta-2,6-dienyloxy}-2-hydroxybenzoic acid, 3-{(2E)-3,7-dimethylocta-2,6-dienyloxy}-5-hydroxybenzoic acid, 2-hydroxy-4-{(2E,6E)-3,7,11-trimethyl-2,6,10-dodecatrienyl}benzoic acid, 4-{(2E)-3,7-dimethylocta-2,6-dienyloxy}-3-methoxybenzoic acid, 2-acetoxy-4-{(2E)-3,7-dimethylocta-2,6-dienyloxy}benzoic acid, N-(2-hydroxyethyl)-4-{(2E)-3,7-dimethylocta-2,6-dienyloxy}-2-hydroxybenzamide, and N-{(2E)-3,7-dimethylocta-2,6-dienyl}-4-amino-2-hydroxybenzoic acid.

6. A novel benzoic acid derivative represented by formula (II):

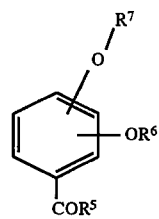

wherein R⁵ represents —OH, —OR⁸ or —NHR⁸; R⁶ represents a hydrogen atom, a lower alkyl group or a lower acyl group; R⁷ represents a branched mono-unsaturated alkyl group having from 6 to 10 carbon atoms; and R⁸ represents an alkyl group or a hydroxyalkyl group, or a pharmacologically acceptable salt thereof.

7. A method of inhibiting sebaceous secretion which comprises applying an effective sebaceous inhibiting amount of a compound according claim 6, to the skin of a user.

8. The novel benzoic acid derivative according to claim 6, wherein R⁵ is —OH and R⁶ is H.

9. The novel benzoic acid derivative according to claim 6, which is methyl 4-(3,7-dimethyl-6-octenyloxy)-2-hydroxybenzoate.

10. The novel benzoic acid derivative according to claim 6, which is 4-(3,7-dimethyl-6-octenyloxy)-2-hydroxybenzoic acid.

11. A novel benzoic acid derivative represented by formula (III):

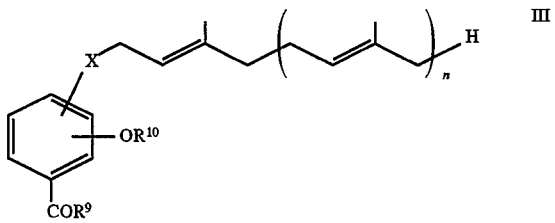

wherein R⁹ represents —OH, —OR¹¹ or —NHR¹¹; R¹⁰ represents a hydrogen atom, a lower alkyl group or a lower acyl group; R¹¹ represents an alkyl group, an alkenyl group or a hydroxyalkyl group; X represents —O— or —NH—; and n represents 1 or 2,
or a pharmacologically acceptable salt thereof.

12. A method of inhibiting sebaceous secretion which comprises applying an effective sebaceous inhibiting amount of a compound according claim 11, to the skin of a user.

13. The novel benzoic acid derivative according to claim 11, wherein X represents —NH—.

14. The novel benzoic acid derivative according to claim 11, wherein R⁹ is —OH and R¹⁰ is H.

15. A benzoic acid derivative represented by formula (II):

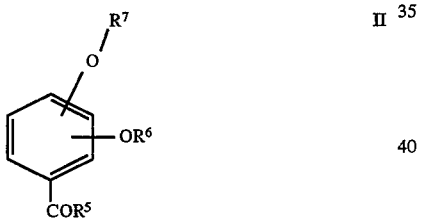

wherein R⁵ represents —OH, —OR⁸, or —NHR⁸; R⁶ represents a hydrogen atom, a lower alkyl group or a lower acyl group; R⁷ represents a branched saturated alkyl group having 6 to 10 carbon atoms; and R⁸ represents an alkyl group or a hydroxyalkyl group; or a pharmacologically acceptable salt thereof.

16. A method of inhibiting sebaceous secretion which comprises applying an effective sebaceous inhibiting amount of a compound according claim 15, to the skin of a user.

17. The benzoic acid derivative according to claim 15 which is methyl 4-(2-ethylhexyloxy)-2-hydroxybenzoate.

18. The benzoic acid derivative according to claim 15 which is methyl 2-hydroxy-4-(3,5,5-trimethylhexyloxy)benzoate.

19. The benzoic acid derivative according to claim 15 which is methyl 5-(2-ethylhexyloxy)-2-hydroxybenzoate.

20. The benzoic acid derivative according to claim 15 which is methyl 2-hydroxy-5-(3,5,5-trimethylhexyloxy)benzoate.

21. The benzoic acid derivative according to claim 15 which is ethyl 3-(2-ethylhexyloxy)-5-hydroxybenzoate.

22. The benzoic acid derivative according to claim 15 which is 4-(2-ethylhexyloxy)-2-hydroxybenzoic acid.

23. The benzoic acid derivative according to claim 15 which is 2-hydroxy-4-(3,5,5-trimethylhexyloxy)benzoic acid.

24. The benzoic acid derivative according to claim 15 which is 5-(2-ethylhexyloxy)-2-hydroxybenzoic acid.

25. The benzoic acid derivative according to claim 15 which is 2-hydroxy-5-(3,5,5-trimethylhexyloxy)benzoic acid.

26. The benzoic acid derivative according to claim 15 which is 3-(2-ethylhexyloxy)-5-hydroxybenzoic acid.

27. The benzoic acid derivative according to claim 15 which is N-(2-hydroxyethyl)-4-(2-ethylhexyloxy)-2-hydroxybenzamide.

28. The benzoic acid derivative according to claim 15 which is N-ethyl-4-(2-ethylhexyloxy)-2-hydroxybenzamide.

29. The benzoic acid derivative according to claim 15 which is sodium 4-(2-ethylhexyloxy)-2-hydroxybenzoate.

30. A benzoic acid derivative represented by formula (II):

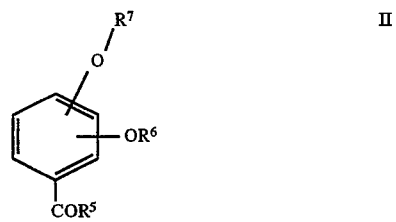

wherein R⁵ represents —OH, —OR⁸, or —NHR⁸; R⁶ represents a hydrogen atom, a lower alkyl group or a lower acyl group; R⁷ represents a cycloalkylalkyl group having 6 to 10 carbon atoms; and R⁸ represents an alkyl group or a hydroxyalkyl group; or a pharmacologically acceptable salt thereof.

31. A method of inhibiting sebaceous secretion which comprises applying an effective sebaceous inhibiting amount of a compound according claim 30, to the skin of a user.

32. The benzoic acid derivative according to claim 30 which is selected from the group consisting of methyl 4-cyclohexylmethoxy-2-hydroxybenzoate, methyl 4-(2-cyclohexylethoxy)-2-hydroxybenzoate, methyl 5-(2-cyclohexylethoxy)-2-hydroxybenzoate, 4-cyclohexylmethoxy-2-hydroxybenzoic acid, 4-(2-cyclohexylethoxy)-2-hydroxybenzoic acid, 5-(2-cyclohexylethoxy)-2-hydroxybenzoic acid, and 2-acetoxy-4-cyclohexylmethoxybenzoic acid.

* * * * *